(12) United States Patent
Brans et al.

(10) Patent No.: US 9,689,021 B2
(45) Date of Patent: Jun. 27, 2017

(54) METHOD FOR MEASURING BETA-LACTAM ANTIBIOTICS

(71) Applicants: UNIVERSITÉ DE LIÈGE, Angleur (BE); UNIVERSITÉ CATHOLIQUE DE LOUVAIN, Louvain-la-Neuve (BE); UNIVERSITÉ LIBRE DE BRUXELLES, Brussels (BE); UNIVERSITÉ DE MONS-HAINAUT, Mons (BE)

(72) Inventors: Alain Brans, Beaufays (BE); Bernard Joris, Louveigne (BE); Michael Delmarcelle, Walhain (BE); Jacqueline Marchand, Braine l'Alleud (BE); Paul Tulkens, Nivelles (BE); Catherine Hammaecher, Pinon (FR); Erik Goormaghtigh, Enghien (BE); Joel De Coninck, Mesvin (BE)

(73) Assignees: UNIVERSITÉ DE LIÈGE, Angleur (BE); UNIVERSITÉ CATHOLIQUE DE LOUVAIN, Louvain-la-Neuve (BE); UNIVERSITÉ LIBRE DE BRUXELLES, Brussels (BE); UNIVERSITÉ DE MONS-HAINAUT, Mons (BE)

( * ) Notice: Subject to any disclaimer, the term of this patent is extended or adjusted under 35 U.S.C. 154(b) by 0 days.

(21) Appl. No.: 14/350,646

(22) PCT Filed: Oct. 15, 2012

(86) PCT No.: PCT/EP2012/070434
§ 371 (c)(1),
(2) Date: Apr. 9, 2014

(87) PCT Pub. No.: WO2013/053953
PCT Pub. Date: Apr. 18, 2013

(65) Prior Publication Data
US 2014/0243241 A1 Aug. 28, 2014

(30) Foreign Application Priority Data
Oct. 14, 2011 (EP) ..................... 11185288

(51) Int. Cl.
G01N 33/94 (2006.01)
C12Q 1/34 (2006.01)
C12N 9/86 (2006.01)

(52) U.S. Cl.
CPC .......... *C12Q 1/34* (2013.01); *C12N 9/86* (2013.01); *G01N 33/9446* (2013.01); *G01N 2333/986* (2013.01)

(58) Field of Classification Search
CPC ... C12Q 1/04; C12Q 1/00; C12Q 1/34; G01N 33/9446; G01N 2333/986
USPC .................................... 435/18, 177
See application file for complete search history.

(56) References Cited

U.S. PATENT DOCUMENTS

| | | | | |
|---|---|---|---|---|
| 3,063,916 A * | 11/1962 | Kosikowski | ..................... | 435/32 |
| 3,941,658 A * | 3/1976 | Lameris et al. | ................ | 435/32 |
| 4,012,518 A * | 3/1977 | Krohn | .................. | C07D 499/00 514/192 |
| 4,239,745 A * | 12/1980 | Charm | ..................... | C12Q 1/18 422/412 |
| 4,379,920 A * | 4/1983 | Brown | .................... | C12P 35/08 540/221 |
| 4,381,343 A * | 4/1983 | Citri | ........................ | C12Q 1/18 435/18 |
| 4,520,101 A * | 5/1985 | Lowe | ...................... | C12P 35/06 435/197 |
| 4,546,076 A * | 10/1985 | Degelaen | ............... | C12N 11/08 435/180 |
| 4,578,377 A * | 3/1986 | Labeeuw | ............ | C07D 501/36 514/206 |
| 4,762,782 A * | 8/1988 | Goldberg | ........... | G01N 33/9446 435/188 |
| 4,847,200 A * | 7/1989 | Wolfe | ................ | C07K 5/06139 435/169 |

(Continued)

FOREIGN PATENT DOCUMENTS

| | | | |
|---|---|---|---|
| EP | 0134078 A2 | 3/1985 | |
| EP | 1710318 A1 * | 10/2006 | ............... C12Q 1/04 |

(Continued)

OTHER PUBLICATIONS

Marshall, Monica J et al, Applied Microbiology, Apr. 1972, vol. 23(4), pp. 765-769, Comparison of the substrate specificities of the B-lactamases from Klebsiella aerogenes 1082E and Enterobacter cloacae P99.*
Weltzien, Hans U. et al, Journal of Invest. Dermatology, vol. 110, pp. 203-206, 1998, Molecular features of Penicillin Allergy.*
Philippon, Alain et al, Antimicrobial Agents and Chemotherapy, Jan. 2002, pp. 1-11, vol. 46(1), Plasmid-Determined AmpC-Type B-lactamases.*
Trepanier, Sonia et al, antimicrobial Agents and Chemotherapy, Mar. 199, p. 543-548, vol. 43(3), Structure-Function Studies ofSer-289 in the Class C B-Lactamase from Enterobacter cloacae P99.*
Henderson, Thomas A et al, Journal of Bacteriology, Oct. 1997, pp. 6112-6121, vol. 179(19), AmpC and AmpH, Proteins Related to the Class C B-lactamases, Bind Penicillin and Contribute to the Normal Morphology of *Escherichia coli*.*
Reybroock, W. et al, Food Additives & Contaminants:Part A, vol. 27:8, pp. 1084-1095, Validation of the Beta-s.t.a.r. 1+1 for rapid screening of residues of B-lactam antibiotics in milk.*

(Continued)

*Primary Examiner* — Padma V Baskar
(74) *Attorney, Agent, or Firm* — James H. Velema, Esq.

(57) ABSTRACT

The present invention relates to methods for determining the concentration of a free beta-lactam antibiotic in a biological sample. In particular, the present invention relates to methods for measuring a free beta-lactam antibiotic in a biological sample, comprising the steps of: (a) providing at least one class C beta-lactamase, a functional fragment or variant thereof; (b) providing at least one biological sample; (c) contacting said at least one class C beta-lactamase with said at least one biological sample; and (d) determining the concentration of said free beta-lactam antibiotic in said at least one biological sample.

10 Claims, 8 Drawing Sheets

(56) References Cited

U.S. PATENT DOCUMENTS

| | | | | |
|---|---|---|---|---|
| 4,888,279 A * | 12/1989 | Zeiger | G01N 33/5308 435/32 |
| 4,978,613 A * | 12/1990 | Bieniarz | C12Q 1/34 435/18 |
| 5,073,484 A * | 12/1991 | Swanson et al. | 435/7.92 |
| 5,128,240 A * | 7/1992 | Shah | G01N 33/53 435/7.1 |
| 5,173,434 A * | 12/1992 | Morris et al. | 436/172 |
| 5,246,830 A * | 9/1993 | Degelaen | C07K 5/06086 435/184 |
| 5,434,053 A * | 7/1995 | Piasio | G01N 33/04 435/28 |
| 5,591,599 A * | 1/1997 | Chang | C12M 41/46 435/29 |
| 5,641,623 A * | 6/1997 | Martin | C07D 277/06 424/1.69 |
| 6,063,589 A * | 5/2000 | Kellogg | B01F 13/0059 366/DIG. 3 |
| 6,120,986 A * | 9/2000 | Martin | C07D 277/06 435/18 |
| 6,280,981 B1 * | 8/2001 | Dykens et al. | 435/110 |
| 6,284,461 B1 * | 9/2001 | Zlokarnik | C12Q 1/34 435/18 |
| 6,319,466 B1 * | 11/2001 | Markovsky | A23D 9/00 422/187 |
| 6,436,649 B1 * | 8/2002 | Kohl | C12Q 1/34 422/504 |
| 6,524,804 B2 * | 2/2003 | Degelaen | G01N 33/54366 435/174 |
| 6,524,865 B1 * | 2/2003 | Martin | C07F 15/0053 435/18 |
| 6,608,046 B1 * | 8/2003 | Besterman | C07F 9/096 423/302 |
| 7,029,868 B2 * | 4/2006 | Sullivan et al. | 435/18 |
| 7,323,303 B2 * | 1/2008 | Wong | G01N 33/573 435/231 |
| 8,071,761 B2 * | 12/2011 | Tsien et al. | 540/222 |
| 8,106,155 B2 * | 1/2012 | Degelaen | G01N 33/54366 435/174 |
| 8,153,390 B2 * | 4/2012 | Bradshaw et al. | 435/15 |
| 9,138,490 B2 * | 9/2015 | Cirillo | A61K 49/0021 |
| 2001/0006820 A1 * | 7/2001 | Knapp et al. | 436/172 |
| 2002/0127737 A1 * | 9/2002 | Degelaen | G01N 33/54366 436/514 |
| 2002/0164639 A1 * | 11/2002 | Degelaen | G01N 33/54366 435/7.1 |
| 2002/0192715 A1 * | 12/2002 | Degelaen | G01N 33/54366 435/7.1 |
| 2003/0036108 A1 * | 2/2003 | Sullivan et al. | 435/23 |
| 2003/0119085 A1 * | 6/2003 | Tsien et al. | 435/32 |
| 2003/0143653 A1 * | 7/2003 | McConnell | C07D 499/00 435/7.32 |
| 2003/0219783 A1 * | 11/2003 | Puglisi et al. | 435/6 |
| 2003/0235877 A1 * | 12/2003 | Kohl | C12Q 1/34 435/7.92 |
| 2004/0067929 A1 * | 4/2004 | Pfaendler | A61K 9/0014 514/210.06 |
| 2004/0096356 A1 * | 5/2004 | Degelaen | G01N 33/558 422/400 |
| 2004/0157262 A1 * | 8/2004 | Kohl et al. | 435/7.1 |
| 2004/0175765 A1 * | 9/2004 | Singh | C12Q 1/6897 435/7.2 |
| 2005/0186197 A1 * | 8/2005 | Palzkill | C07K 7/06 424/94.3 |
| 2005/0227309 A1 * | 10/2005 | Corry | C07D 499/00 435/32 |
| 2005/0261270 A1 * | 11/2005 | Wong | G01N 33/573 514/210.02 |
| 2006/0029994 A1 * | 2/2006 | Chou et al. | 435/34 |
| 2006/0178357 A1 * | 8/2006 | Buynak | C07D 501/14 514/200 |
| 2007/0161040 A1 * | 7/2007 | Giannotta | C07K 14/245 435/7.1 |
| 2008/0009029 A1 * | 1/2008 | Govorun | C12Q 1/18 435/32 |
| 2009/0023170 A1 * | 1/2009 | Citri | 435/18 |
| 2009/0275065 A1 * | 11/2009 | Xing et al. | 435/18 |
| 2010/0022504 A1 * | 1/2010 | Mainardi | A61K 31/397 514/210.05 |
| 2010/0285503 A1 * | 11/2010 | Bradshaw et al. | 435/7.5 |
| 2010/0285572 A1 * | 11/2010 | Salter et al. | 435/287.3 |
| 2011/0112059 A1 * | 5/2011 | Hasan | C07D 501/52 514/209 |
| 2011/0245105 A1 * | 10/2011 | Citri | C12Q 1/04 506/10 |
| 2012/0245128 A1 * | 9/2012 | Haag | G01N 33/15 514/90 |
| 2013/0095511 A1 * | 4/2013 | Kostrzewa | C12Q 1/34 435/18 |

FOREIGN PATENT DOCUMENTS

| | | | | |
|---|---|---|---|---|
| WO | 97/41435 | * | 11/1997 | G01N 33/53 |
| WO | 02/32423 | * | 4/2002 | A61K 31/424 |
| WO | 2009/051838 | * | 4/2009 | C12Q 1/04 |
| WO | 2009/137062 | * | 11/2009 | C12Q 1/34 |

OTHER PUBLICATIONS

Kumar, Sanjai etal, Biochemistry, 2004,vol. 43, pp. 2664-2672, Kinetics of Turnover of Cefotaxime by the Enterobacter cloacae P99 and GC1 B-Lactamases: Two Free Enzyme forms of the P99 B-Lactamase Detected by a Combination ofPre- and Post Steady State Kinetcs.*

O'Callaghan, Cynthia H et al, Journal of Bacteriology, Jun. 1972, pp. 988-991, vol. 110(3), Correlation Between hydrolysis of the B-lactam bond of the Cephalosporin Nucleus and Expulsion of the 3-Substituent.*

Movassagh, Mohammad Hosein, Scholars Research Library, annals of Biological Ressearch, 2011, vol. 2(2), p. 95-98, Detection of Beta Lactam Antibiotics Residues in Iranian Ultra High Temperature Milk by Beta Star Test.*

Puckett, Libby G et al, Analytical Biochemistry, vol. 309, pp. 224-231, 2002, Development of an assay for B-lactam hydrolysis using the pH dependenc of enhanced green fluorescent protein.*

Angelidis, AS et al, Journal of Food Protection, vol. 62(10), 1999, pp. 1183-1190, Evaluation of the Delvo-X-Press Assay for Detecting Antibiotic Residues in Milk Samples from Individual Cows.*

Berruga, MI et al, Journal of Food Protection, vol. 66(11), 2003, pp. 2097-2102, Performances of Antibiotic Screening Tests in Determining the Persistence of Penicillin Residues in Ewe's Milk.*

Reybroeck, W. 2008, Bull. IDF, vol. 428, pp. 13-16, The use of microbiological, immunologocial and receptor tests for monitoring of residues of antimicrobials in milk: The Belgian approach.*

Reybroeck, W, 2000. Paper presented at $2^{nd}$ International Food SENSE Workshop, Mar. 30-Apr. 2, 2000, one page, Zeven Germany, Evaluation of the Beta-s.t.a.r. for the detection of B-lactam antibiotics.*

International Preliminary Report on Patentability and Written Opinion for International Application No. PCT/EP2012/070434. Dated Apr. 15, 2014. 9 pages.

Galleni et al. 'A Survey of the Kinetic Parameters of Class C β-Lactamases' Biochemical Journal. 1988, vol. 255, No. 1, pp. 123-129.

Ambler RP. The structure of β-lactamases. Philos Trans R Soc Lond B Biol Sci 1980; 289: 321-31.

Bush. 'Characterization of beta-lactamases'. Antimicrob Agents Chemother. 1989 vol. 33, No. 3, pp. 259-263.

Keana, John FW, and Sui Xiong Cai. "New reagents for photoaffinity labeling: synthesis and photolysis of functionalized perfluorophenyl azides." The Journal of Organic Chemistry 55.11 (1990): 3640-3647.

Goldzstein, Andréa, et al. "Ligand—receptor interactions in complex media: A new type of biosensors for the detection of coagulation factor VIII." Biosensors and Bioelectronics 24.7 (2009): 1831-1836.

(56) References Cited

OTHER PUBLICATIONS

Liu et al. (2010) "Metallic nanoparticles bioassay for Enterobacter cloacae P99 β-lactamase activity and inhibitor screening," Analyst. 135:1031-1036.

Wong et al. (2011) "Structural studies of the mechanism for biosensing antibiotics in a fluorescein-labeled β-lactamase," BMC Structural Biology. 11(15):1-8.

Urbach et al. (2008) "A new family of cyanobacterial penicillin-binding proteins. A missing link in the evolution of class A beta-lactamases." J. Bio. Chem., 283(47):32516-32526.

Lamotte-Brasseur et al. (1991) "Mechanism of acyl transfer by the class A serine beta-lactamase of Streptomyces albus G." Biochem. J., 279:213-221.

Guillaume et al. (1997) "Site-directed mutagenesis of glutamate 166 in two beta-lactamases. Kinetic and molecular modeling studies." J. Biol. Chem., 272(9):5438-5444.

Beta-lactamase. (Jul. 29, 2015). Retrieved from wikipedia.org/wiki/Beta-lactamase.

\* cited by examiner

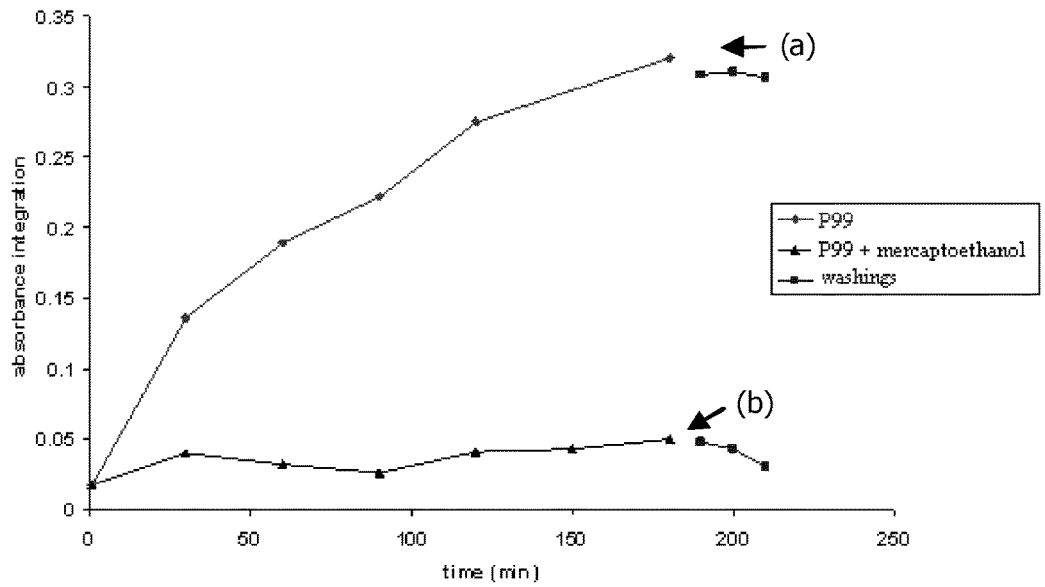

(SEQ ID No. 5)
ATGGCGCCAGTGTCAGAAAAACAGCTGGCGGAGGTGGTCGCGAATACGATTACCCCGCTGATGAAAGCCC
AGTCTGTTCCAGGCATGGCGGTGGCCGTTATTTATCAGGGAAAACCGCACTATTACACATTTGGCAAGGC
CGATATCGCGGCGAATAAACCCGTTACGCCTCAGACCCTGTTCGAGCTGGGTTCTATAAGTAAAACCTTC
ACCGGCGTTTTAGGTGGGGATGCCATTGCTCGCGGTGAAATTTCGCTGGACGATGCGGTGACCAGATACT
GGCCACAGCTGACGGGCAAGCAGTGGCAGGGTATTCGTATGCTGGATCTCGCCACCTACACCGCTGGCGG
CCTGCCGCTACAGGTACCGGATGAGGTCACGGATAACGCCTCCCTGCTGCGCTTTTATCAAAACTGGCAG
CCGCAGTGGAAGCCTGGCACAACGCGTCTTTACGCCAACGCCAGCATCGGTCTTTTTGGTGCGCTGGCGG
TCAAACCTTCTGGCATGCCCTATGAGCAGGCCATGACGACGCGGGTCCTTAAGCCGCTCAAGCTGGACCA
TACCTGGATTAACGTGCCGAAAGCGGAAGAGGCGCATTACGCCTGGGGCTATCGTGACGGTAAAGCGGTG
CGCGTTTCGCCGGGTATGCTGGATGCACAAGCCTATGGCGTGAAAACCAACGTGCAGGATATGGCGAACT
GGGTCATGGCAAACATGGCGCCGGAGAACGTTGCTGATGCCTCACTTAAGCAGGGCATCGCGCTGGCGCA
GTCGCGCTACTGGCGTATCGGGTCAATGTATCAGGGTCTGGGCTGGGAGATGCTCAACTGGCCCGTGGAG
GCCAACACGGTGGTCGAGGGCAGCGACAGTAAGGTAGCACTGGCGCCGTTGCCCGTGGCAGAAGTGAATC
CACCGGCTCCCCCGGTCAAAGCGTCCTGGGTCCATAAAACGGGCTCTACTGGCGGGTTTGGCAGCTACGT
GGCCTTTATTCCTGAAAAGCAGATCGGTATTGTGATGCTCGCGAATACAAGCTATCCGAACCCGGCACGC
GTTGAGGCGGCATACCATATCCTTGAGGCGCTCGAGCACCACCACCACCACCACTGA

FIG. 6

(SEQ ID No. 6)
MAPVSEKQLAEVVANTITPLMKAQSVPGMAVAVIYQGKPHYYTFGKADIAANKPVTPQTLFELGSISKTF
TGVLGGDAIARGEISLDDAVTRYWPQLTGKQWQGIRMLDLATYTAGGLPLQVPDEVTDNASLLRFYQNWQ
PQWKPGTTRLYANASIGLFGALAVKPSGMPYEQAMTTRVLKPLKLDHTWINVPKAEEAHYAWGYRDGKAV
RVSPGMLDAQAYGVKTNVQDMANWVMANMAPENVADASLKQGIALAQSRYWRIGSMYQGLGWEMLNWPVE
ANTVVEGSDSKVALAPLPVAEVNPPAPPVKASWVHKTGSTGGFGSYVAFIPEKQIGIVMLANTSYPNPAR
VEAAYHILEALEHHHHHH

FIG. 7
(SEQ ID No. 7)
ATGGCGCCAGTGTCAGAAAAACAGCTGGCGGAGGTGGTCGCGAATACGATTACCCCGCTGATGAAAGCCC
AGTCTGTTCCAGGCATGGCGGTGGCCGTTATTTATCAGGGAAAAACCGCACTATTACACATTTGGCAAGGC
CGATATCGCGGCGAATAAACCCGTTACGCCTCAGACCCTGTTCGAGCTGGGTTCTATAAGTAAAACCTTC
ACCGGCGTTTTAGGTGGGGATGCCATTGCTCGCGGTGAAATTTCGCTGGACGATGCGGTGACCAGATACT
GGCCACAGCTGACGGGCAAGCAGTGGCAGGGTATTCGTATGCTGGATCTCGCCACCTACACCGCTGGCGG
CCTGCCGCTACAGGTACCGGATGAGGTCACGGATAACGCCTCCCTGCTGCGCTTTTATCAAAACTGGCAG
CCGCAGTGGAAGCCTGGCACAACGCGTCTTTACGCCAACGCCAGCATCGGTCTTTTTGGTGCGCTGGCGG
TCAAACCTTCTGGCATGCCCTATGAGCAGGCCATGACGACGCGGGTCCTTAAGCCGCTCAAGCTGGACCA
TACCTGGATTAACGTGCCGAAAGCGGAAGAGGCGCATTACGCCTGGGGCTATCGTGACGGTAAAGCGGTG
CGCGTTTCGCCGGGTATGCTGGATGCACAAGCCTATGGCGTGAAAACCAACGTGCAGGATATGGCGAACT
GGGTCATGGCAAACATGGCGCCGGAGAACGTTGCTGATTGCTCACTTAAGCAGGGCATCGCGCTGGCGCA
GTCGCGCTACTGGCGTATCGGGTCAATGTATCAGGGTCTGGGCTGGGAGATGCTCAACTGGCCCGTGGAG
GCCAACACGGTGGTCGAGGGCAGCGACAGTAAGGTAGCACTGGCGCCGTTGCCCGTGGCAGAAGTGAATC
CACCGGCTCCCCCGGTCAAAGCGTCCTGGGTCCATAAAACGGGCTCTACTGGCGGGTTTGGCAGCTACGT
GGCCTTTATTCCTGAAAAGCAGATCGGTATTGTGATGCTCGCGAATACAAGCTATCCGAACCCGGCACGC
GTTGAGGCGGCATACCATATCCTTGAGGCGCTCGAGCACCACCACCACCACCACTGA

FIG. 8
(SEQ ID No. 8)
MAPVSEKQLAEVVANTITPLMKAQSVPGMAVAVIYQGKPHYYTFGKADIAANKPVTPQTLFELGSISKTF
TGVLGGDAIARGEISLDDAVTRYWPQLTGKQWQGIRMLDLATYTAGGLPLQVPDEVTDNASLLRFYQNWQ
PQWKPGTTRLYANASIGLFGALAVKPSGMPYEQAMTTRVLKPLKLDHTWINVPKAEEAHYAWGYRDGKAV
RVSPGMLDAQAYGVKTNVQDMANWVMANMAPENVADCSLKQGIALAQSRYWRIGSMYQGLGWEMLNWPVE
ANTVVEGSDSKVALAPLPVAEVNPPAPPVKASWVHKTGSTGGFGSYVAFIPEKQIGIVMLANTSYPNPAR
VEAAYHILEALEHHHHHH

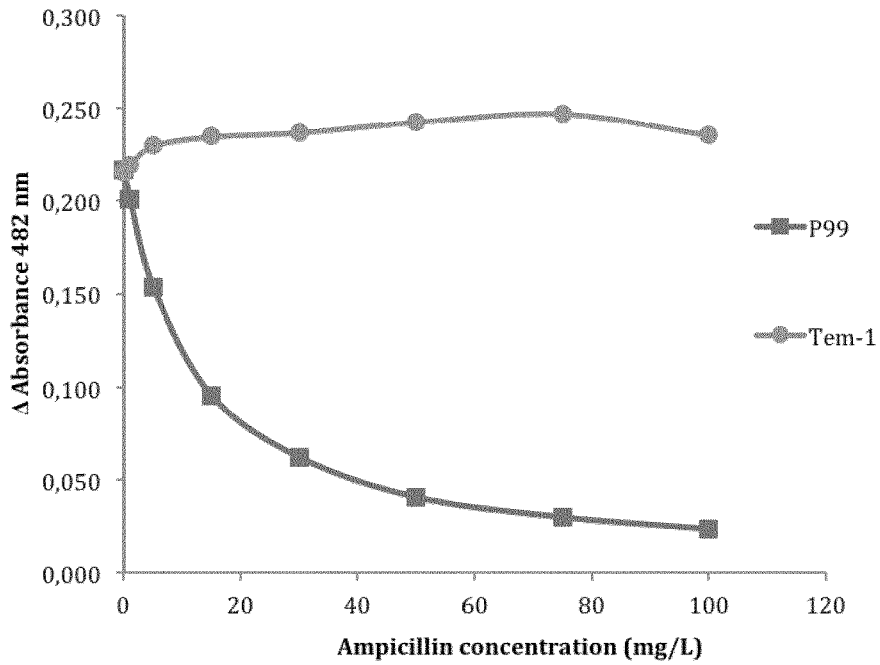

FIG. 9

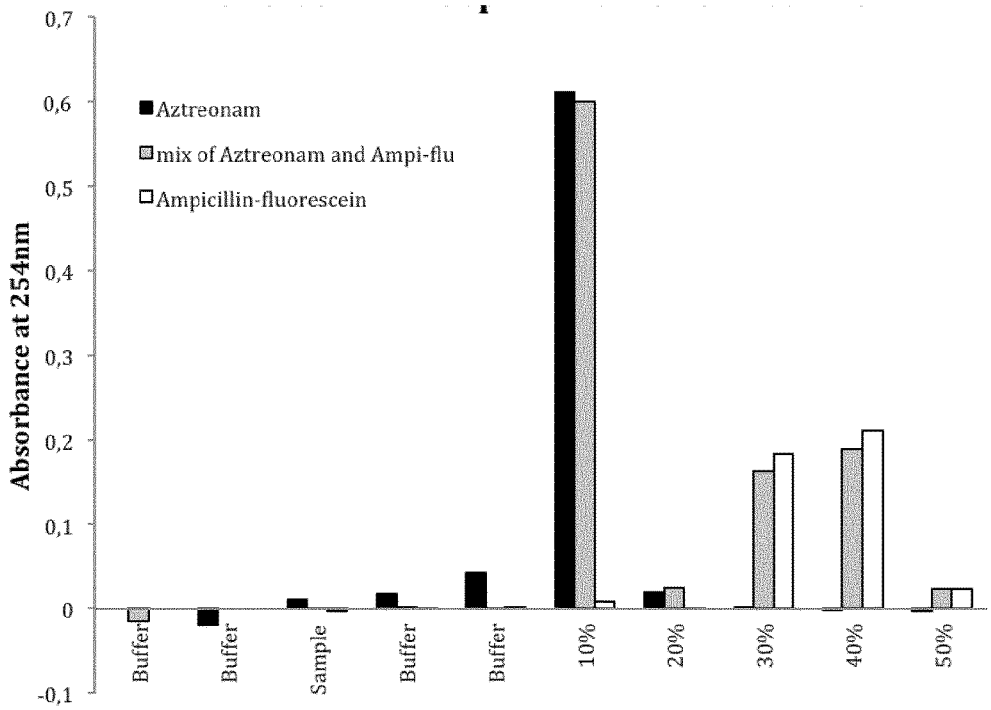

(SEQ ID No. 9)
ATGATGAGAAAATCCCTTTGCTGCGCCCTGCTGCTCGGCATCTCTTGCTCTGCTCTCGCCACGCCAGTGTCAG
AAAAACAGCTGGCGGAGGTGGTCGCGAATACGATTACCCCGCTGATGAAAGCCCAGTCTGTTCCAGGCATGGC
GGTGGCCGTTATTTATCAGGGAAAACCGCACTATTACACATTTGGCAAGGCCGATATCGCGGCGAATAAACCC
GTTACGCCTCAGACCCTGTTCGAGCTGGGGTTCTATAAGTAAAACCTTCACCGGCGTTTTAGGTGGGGATGCCA
TTGCTCGCGGTGAAATTTCGCTGGACGATGCGGTGACCAGATACTGGCCACAGCTGACGGGCAAGCAGTGGCA
GGGTATTCGTATGCTGGATCTCGCCACCTACACCGCTGGCGGCCTGCCGCTACAGGTACCGGATGAGGTCACG
GATAACGCCTCCCTGCTGCGCTTTTATCAAAACTGGCAGCCGCAGTGGAAGCCTGGCACAACGCGTCTTTACG
CCAACGCCAGCATCGGTCTTTTTGGTGCGCTGGCGGTCAAACCTTCTGGCATGCCCTATGAGCAGGCCATGAC
GACGCGGGTCCTTAAGCCGCTCAAGCTGGACCATACCTGGATTAACGTGCCGAAAGCGGAAGAGGCGCATTAC
GCCTGGGGCTATCGTGACGGTAAAGCGGTGCGCGTTTCGCCGGGTATGCTGGATGCACAAGCCTATGGCGTGA
AAACCAACGTGCAGGATATGGCGAACTGGGTCATGGCAAACATGGCGCCGGAGAACGTTGCTGATGCCTCACT
TAAGCAGGGCATCGCGCTGGCGCAGTCGCGCTACTGGCGTATCGGGTCAATGTATCAGGGTCTGGGCTGGGAG
ATGCTCAACTGGCCCGTGGAGGCCAACACGGTGGTCGAGGGCAGCGACAGTAAGGTAGCACTGGCGCCGTTGC
CCGTGGCAGAAGTGAATCCACCGGCTCCCCCGGTCAAAGCGTCCTGGGTCCATAAAACGGGCTCTACTGGCGG
GTTTGGCAGCTACGTGGCCTTTATTCCTGAAAAGCAGATCGGTATTGTGATGCTCGCGAATACAAGCTATCCG
AACCCGGCACGCGTTGAGGCGGCATACCATATCCTCGAGGCGCTACAGTAA

FIG. 12

(SEQ ID No. 10)
MMRKSLCCALLLGISCSALATPVSEKQLAEVVANTITPLMKAQSVPGMAVAVIYQGKPHYYTFGKADIAANKP
VTPQTLFELGSISKTFTGVLGGDAIARGEISLDDAVTRYWPQLTGKQWQGIRMLDLATYTAGGLPLQVPDEVT
DNASLLRFYQNWQPQWKPGTTRLYANASIGLFGALAVKPSGMPYEQAMTTRVLKPLKLDHTWINVPKAEEAHY
AWGYRDGKAVRVSPGMLDAQAYGVKTNVQDMANWVMANMAPENVADASLKQGIALAQSRYWRIGSMYQGLGWE
MLNWPVEANTVVEGSDSKVALAPLPVAEVNPPAPPVKASWVHKTGSTGGFGSYVAFIPEKQIGIVMLANTSYP
NPARVEAAYHILEALQ

FIG. 13
(SEQ ID No. 11)
ATGATGAGAAAATCCCTTTGCTGCGCCCTGCTGCTCGGCATCTCTTGCTCTGCTCTCGCCACGCCAGTGTCAG
AAAAACAGCTGGCGGAGGTGGTCGCGAATACGATTACCCCGCTGATGAAAGCCCAGTCTGTTCCAGGCATGGC
GGTGGCCGTTATTTATCAGGGAAAACCGCACTATTACACATTTGGCAAGGCCGATATCGCGGCGAATAAACCC
GTTACGCCTCAGACCCTGTTCGAGCTGGGTTCTATAAGTAAAACCTTCACCGGCGTTTTAGGTGGGGATGCCA
TTGCTCGCGGTGAAATTTCGCTGGACGATGCGGTGACCAGATACTGGCCACAGCTGACGGGCAAGCAGTGGCA
GGGTATTCGTATGCTGGATCTCGCCACCTACACCGCTGGCGGCCTGCCGCTACAGGTACCGGATGAGGTCACG
GATAACGCCTCCCTGCTGCGCTTTTATCAAAACTGGCAGCCGCAGTGGAAGCCTGGCACAACGCGTCTTTACG
CCAACGCCAGCATCGGTCTTTTTGGTGCGCTGGCGGTCAAACCTTCTGGCATGCCCTATGAGCAGGCCATGAC
GACGCGGGTCCTTAAGCCGCTCAAGCTGGACCATACCTGGATTAACGTGCCGAAAGCGGAAGAGGCGCATTAC
GCCTGGGGCTATCGTGACGGTAAAGCGGTGCGCGTTTCGCCGGGTATGCTGGATGCACAAGCCTATGGCGTGA
AAACCAACGTGCAGGATATGGCGAACTGGGTCATGGCAAACATGGCGCCGGAGAACGTTGCTGATTGCTCACT
TAAGCAGGGCATCGCGCTGGCGCAGTCGCGCTACTGGCGTATCGGGTCAATGTATCAGGGTCTGGGCTGGGAG
ATGCTCAACTGGCCCGTGGAGGCCAACACGGTGGTCGAGGGCAGCGACAGTAAGGTAGCACTGGCGCCGTTGC
CCGTGGCAGAAGTGAATCCACCGGCTCCCCCGGTCAAAGCGTCCTGGGTCCATAAAACGGGCTCTACTGGCGG
GTTTGGCAGCTACGTGGCCTTTATTCCTGAAAAGCAGATCGGTATTGTGATGCTCGCGAATACAAGCTATCCG
AACCCGGCACGCGTTGAGGCGGCATACCATATCCTCGAGGCGCTACAGTAA

FIG. 14
(SEQ ID No. 12)
MMRKSLCCALLLGISCSALATPVSEKQLAEVVANTITPLMKAQSVPGMAVAVIYQGKPHYYTFGKADIAANKP
VTPQTLFELGSISKTFTGVLGGDAIARGEISLDDAVTRYWPQLTGKQWQGIRMLDLATYTAGGLPLQVPDEVT
DNASLLRFYQNWQPQWKPGTTRLYANASIGLFGALAVKPSGMPYEQAMTTRVLKPLKLDHTWINVPKAEEAHY
AWGYRDGKAVRVSPGMLDAQAYGVKTNVQDMANWVMANMAPENVADCSLKQGIALAQSRYWRIGSMYQGLGWE
MLNWPVEANTVVEGSDSKVALAPLPVAEVNPPAPPVKASWVHKTGSTGGFGSYVAFIPEKQIGIVMLANTSYP
NPARVEAAYHILEALQ

METHOD FOR MEASURING BETA-LACTAM ANTIBIOTICS

RELATED APPLICATIONS

This application is a 35 U.S.C. §371 filing of International Application No. PCT/EP2012/070434, filed Oct. 15, 2012, which claims priority to European Patent Application No. 11185288.5, filed Oct. 14, 2011, each of which is incorporated herein by reference in its entirety.

FIELD OF THE INVENTION

The invention relates to methods for measuring beta-lactam antibiotics. The invention is particularly important to the monitoring and adjusting of a beta-lactam antibiotic dosage provided to a subject suffering from an infection treatable with beta-lactam antibiotics. The invention further relates to *Enterobacter cloacae* P99 beta-lactamase and its variants.

BACKGROUND OF THE INVENTION

Beta-lactam antibiotics are the most widely used group of antibiotics in the treatment of infections caused by both Gram-positive and Gram-negative bacteria. Antibiotherapies with beta-lactam antibiotics via the so-called "continuous infusion" method is more and more required in hospitals due to the increasing occurrence of complicated infections and bacterial resistances. This is particularly true for patients in services of intensive care, services of orthopedic surgery and pediatric services. For best optimization of the dosing of beta-lactam antibiotics during antibiotherapy, whether by continuous infusion or conventional administration, continuous monitoring and adjustment of the amount delivered to the patient is required. Therefore, it is of paramount importance to be able to rapidly and continuously quantify the concentration of free beta-lactam antibiotics circulating in the patient's blood during antibiotherapy.

In the medical field, the quantitative analysis of beta-lactam antibiotics is performed in clinical laboratories, using mainly microbiological or biochemical (HPLC) assays. Microbiological analyses have the disadvantage that they last a few days and thus rapid follow up of the delivered drug doses is impossible.

In the agro-alimentary field, several methods have been developed for the quantitative analysis of beta-lactam antibiotics, in particular for the quality control of milk. Some of these methods make use of radioactive labeling and disadvantageously require therefore special equipment. Furthermore, these procedures are not without danger for the person performing the analysis. Alternative methods have been described for the quantitative analysis of beta-lactam antibiotics without radioactive labeling; however, these methods do not cover the detection of some important beta-lactam antibiotics used in the medical field. Furthermore, methods have been developed for the detection of beta-lactam antibiotics in milk which make use of a device on which a reference antibiotic is immobilized. The device comprises a solid support whereon several membranes are fixed. Such methods however do not allow the continuous monitoring of beta-lactam antibiotics required during antibiotherapy.

Unfortunately, the concentration of free beta-lactam antibiotics in serum cannot be predicted from the drug doses delivered to the patient. Indeed, serum concentrations of free beta-lactam antibiotics feature great differences and variations from one patient to another, since serious infections are characterized by important disorders in drug distribution and elimination parameters, and in serum protein rates. Consequently, the optimal delivery of beta-lactam antibiotics remains often restricted to a few advanced hospital services because of the difficulty to get rapid measurements of free beta-lactam antibiotics in serum.

Accordingly, a need exists to develop further and improved methods for the quantification of beta-lactam antibiotics in samples, such as complex physiological samples.

SUMMARY OF THE INVENTION

The invention provides technology adapted to the measurement, including quantitative analysis, of a beta-lactam antibiotic.

In a first aspect, the invention provides methods for the measurement of beta-lactam antibiotics. Specifically, the present invention relates to methods for measuring the free concentration of beta-lactam antibiotics in a biological sample, comprising the steps of:
(a) providing at least one class C beta-lactamase, a functional fragment or variant thereof;
(b) providing at least one biological sample;
(c) contacting said at least one class C beta-lactamase with said at least one biological sample; and
(d) measuring said free concentration of beta-lactam antibiotics in said at least one biological sample.

Preferably, the present invention relates to a method for determining the concentration of a free beta-lactam antibiotic in a biological sample, comprising the steps of:
(a) providing at least one class C beta-lactamase, a functional fragment or variant thereof;
(b) providing at least one biological sample;
(c) contacting said at least one class C beta-lactamase with said at least one biological sample; and
(d) determining said concentration of said free beta-lactam antibiotic in said at least one biological sample.

As illustrated in the example section, the inventors have found that the reaction kinetics of class C beta-lactamases can be used for determining the concentration of beta-lactam antibiotics in a biological sample. The method of the present invention ensures a rapid and simple quantitative analysis of free beta-lactam antibiotics in biological samples. Furthermore, the method of the invention advantageously allows online and real-time monitoring of beta-lactam antibiotics in biological samples such as biological fluids such as serum. In particular, the present method allows for the quantification of beta-lactam antibiotics in complex physiological media that is applicable to clinical practice. The present method allows repeated blood level monitoring and rapid delivery of the results to the clinician in order to ensure optimal treatment of a subject.

In a further aspect, the present invention provides a class C beta-lactamase which is a variant of the wild type class C beta-lactamase of *Enterobacter cloacae* P99 which has been modified so as to have the alanine 266 replaced by a cysteine, also referred to herein as P99A266C. In particular, the present invention encompasses a variant of *Enterobacter cloacae* P99 beta-lactamase wherein the alanine at position 266 of P99 lactamase is substituted by a cysteine. More preferably, the present invention encompasses a variant of *Enterobacter cloacae* P99 beta-lactamase wherein the alanine at position 266 of SEQ ID No 12 is substituted by a cysteine.

The class C beta-lactamase allows the measurement and/or quantification of a free beta-lactam antibiotic in a biological sample. The class C beta-lactamase P99A266C advantageously enables immobilization of the class C beta-lactamase. The cysteine present in P99A266C allows coupling the class C beta-lactamase for example with an organic molecule or a multifunctional arm-spacer of a device, both as defined herein. The thiol group present in said cysteine at position 266 in P99A266C is advantageously available in the opposite direction of the active site of the class C beta-lactamase, and does not affect the activity of the enzyme.

The above and other characteristics, features and advantages of the present invention will become apparent from the following detailed description, which illustrate, by way of example, the principles of the invention.

DESCRIPTION OF THE FIGURES

FIG. 1A: Plot of enzyme residual activity (%) as a function of TAZOCIN® (piperacillin) concentration, FIG. 1B: plot of enzyme residual activity (%) as a function of piperacillin concentration, FIG. 1C plot of enzyme residual activity (%) as a function of NEGABAN® (temocillin) concentration and FIG. 1D: plot with standard error of the residual activity (%) as a function of Pentrexyl® (ampicillin) concentration measured on two different days.

FIG. 4C represents a graph measuring the binding of P99A266C enzyme on the N-maleimide-functionalized germanium ATR channel as function of time (shown as the absorbance integration as a function of time) (a) in the absence of mercaptoethanol passivation and (b) after mercaptoethanol passivation of the channel.

FIG. 5 represents a nucleic acid sequence encoding a recombinant class C beta-lactamase of *Enterobacter cloacae* P99 (SEQ ID NO.5, underlined: alanine 247 codon).

FIG. 6 represents an amino acid sequence of a recombinant P99 beta-lactamase (SEQ ID NO.6, underlined: alanine 247).

FIG. 7 represents a nucleic acid sequence encoding a variant of class C beta-lactamase of *Enterobacter cloacae* P99 which has been modified so as to have the alanine 247 replaced by a cysteine (SEQ ID NO. 7, underlined: alanine 247 codon mutated in cysteine codon). The nucleic acid sequence encoding the first 21 amino acids of wild type class C beta-lactamase of *Enterobacter cloacae* P99 have been replaced by a nucleic acid sequence encoding two amino acids (MA).

FIG. 8 represents the amino acid sequence of class C beta-lactamase variant of *Enterobacter cloacae* P99 which has been modified so as to have the alanine 247 replaced by a cysteine (SEQ ID NO. 8, underlined: mutated alanine 247 in cysteine).

FIG. 9 represents a graph illustrating the effect of ampicillin concentration on the rate ($\Delta Abs_{482}$/min) of P99 or Tem-1 catalyzed reaction at fixed concentration of nitrocefin or CPR.

FIG. 10 represents a graph plotting the absorbance at 254 nm of fractions containing either aztreonam, ampicillin-fluorescein, or a mixture thereof, after separation of beta-lactam antibiotics on a C18 column using buffer containing from 10 to 50% acetonitrile; black: aztreonam; gray: mix of aztreonam and ampicillin-fluorescein (ampi-flu); white: ampicillin-fluorescein.

FIG. 11 represents a nucleic acid sequence encoding wild type class C beta-lactamase of *Enterobacter cloacae* P99 (SEQ ID NO.9, underlined: alanine 266 codon).

FIG. 12 represents the amino acid sequence of wild type class C beta-lactamase of *Enterobacter cloacae* P99 (SEQ ID NO.10, underlined: alanine 266).

FIG. 13 represents a nucleic acid sequence encoding a variant of class C beta-lactamase of *Enterobacter cloacae* P99 which has been modified so as to have the alanine 266 replaced by a cysteine (SEQ ID NO. 11, underlined: alanine 266 codon mutated in cysteine codon).

FIG. 14 represents the amino acid sequence of a variant of class C beta-lactamase of *Enterobacter cloacae* P99 which has been modified so as to have the alanine 266 replaced by a cysteine (SEQ ID NO. 12, underlined: mutated alanine 266 in cysteine).

DETAILED DESCRIPTION OF THE INVENTION

Figure 1A:
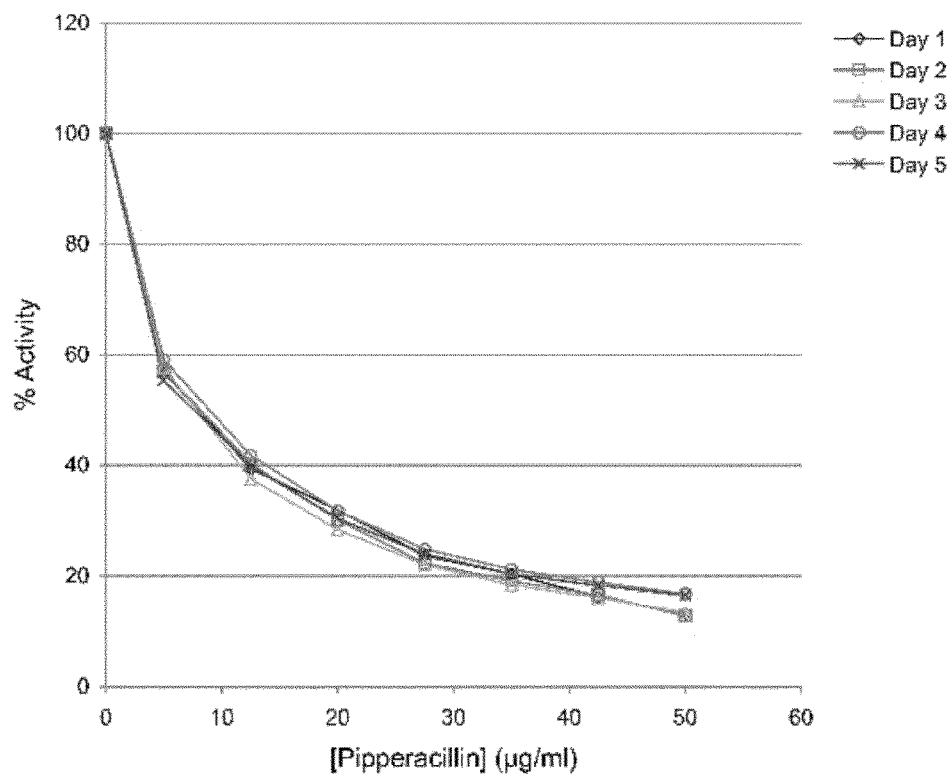
FIGS. 1A, 1B, 1C and 1D represent graphs plotting the residual P99 activity (in percentage) as a function of beta-lactam antibiotics concentrations measured on different days.
Figure 1B:
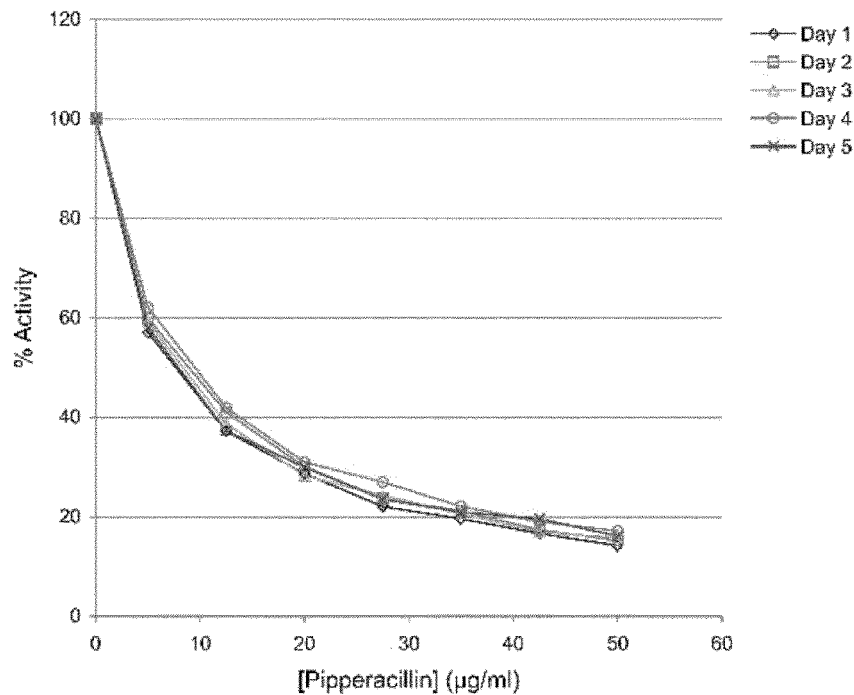
Figure 1C:
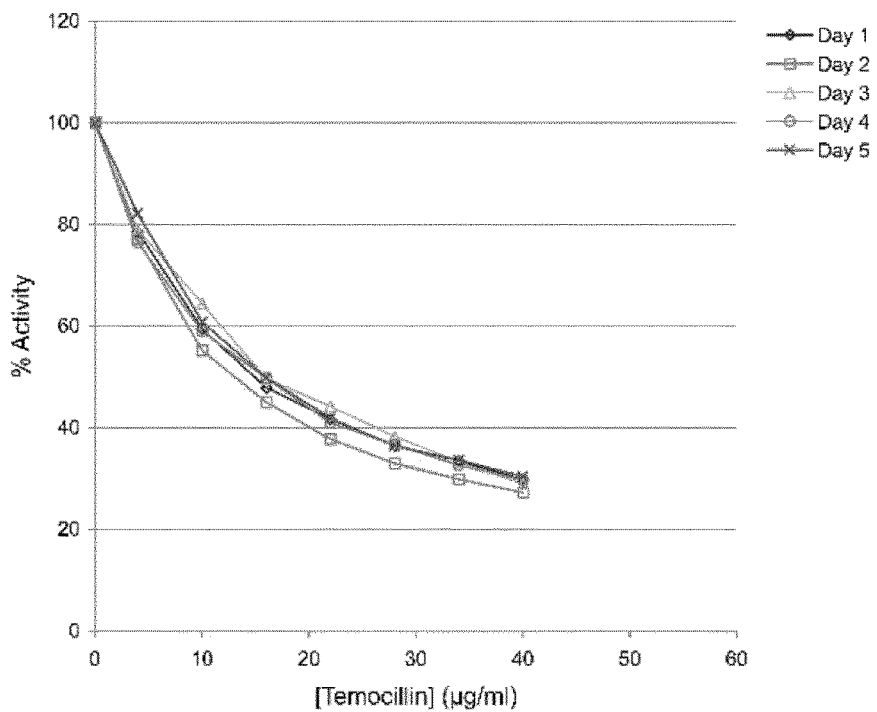
Figure 1D:
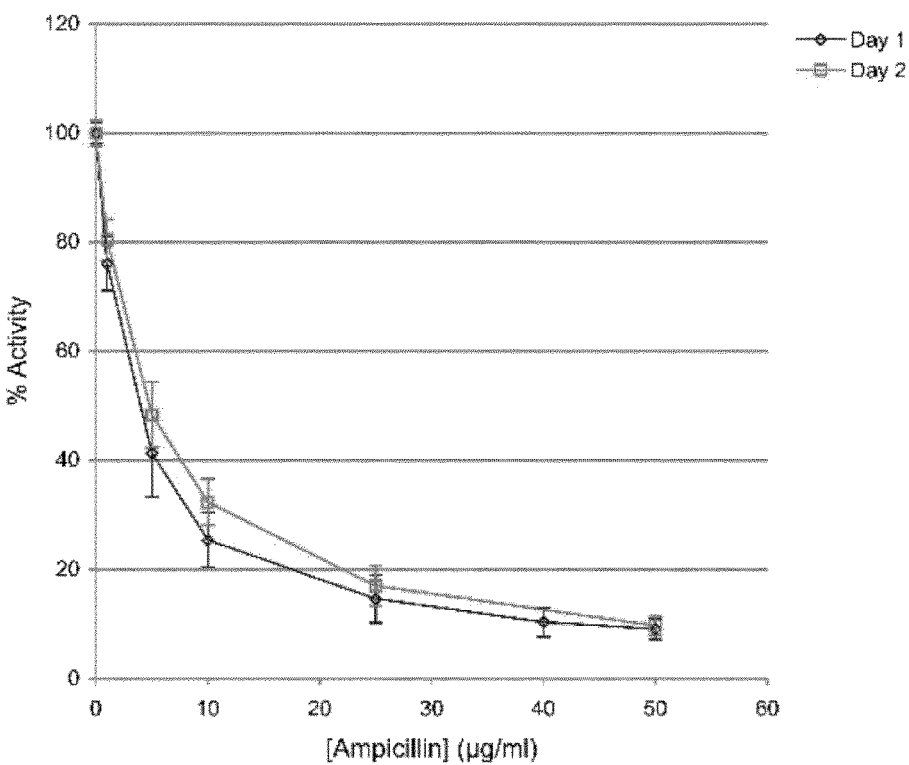

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The present invention relates to an improved method for measuring and/or monitoring the level of free beta-lactam antibiotics in a biological sample.

Preferably, the present invention relates to a method for determining the concentration of one or more free beta-lactam antibiotics in a biological sample, comprising the steps of: providing at least one class C beta-lactamase, a functional fragment or variant thereof; providing at least one biological sample; contacting said at least one class C beta-lactamase with said at least one biological sample; and determining the concentration of said one or more free beta-lactam antibiotics in said at least one biological sample.

The recitation "measuring a beta-lactam antibiotic" generally refers to determining the amount, quantity or concentration of the beta-lactam antibiotic in the sample. The recitation measuring a beta-lactam antibiotic may encompass quantifying and/or monitoring the beta-lactam antibiotic. The term "monitoring" generally refers to measuring the amount or quantity of the beta-lactam antibiotic over time. For instance, monitoring a free beta-lactam antibiotic in a biological sample may be performed by measuring the beta-lactam antibiotic concentration at one or more successive time points.

By the term "free" beta-lactam antibiotic it is meant beta-lactam antibiotic unbound to biological molecules such as proteins.

The term "beta-lactam antibiotic", as used herein, concerns an antibiotic agent that comprises a beta-lactam ring in its molecular structure.

The term "beta-lactam ring" refers to a lactam or cyclic amide structure, as shown in Formula (I).

(I)

The reference herein to beta-lactam antibiotic may encompass one beta-lactam antibiotic or a combination thereof. Hence, the reference herein to measuring (or measuring the quantity of) a beta-lactam antibiotic may encompass measuring one or more beta-lactam antibiotics.

The beta-lactam antibiotic may be selected from the group comprising a penicillin, a cephalosporin, a carbapenem, a penem or a monobactam. In some embodiments, the beta-lactam antibiotic is active against multidrug-resistant microorganisms. In some embodiments, the beta-lactam antibiotic may be selected from the group comprising a penicillin, a cephalosporin, a carbapenem, a penem or a monobactam, wherein said penicillin, cephalosporin, carbapenem, penem or monobactam is active against organisms resistant to one or more of said penicillins, cephalosporins, carbapenems, penems or monobactams, such as beta-lactamase-producing organisms or the Methicillin-resistant *Staphylococcus aureus* (MRSA), also called oxacillin-resistant *Staphylococcus aureus* (ORSA).

The term "penicillin" or "penam" refers to a beta-lactam antibiotic comprising a thiazolidine ring.

The term "cephalosporin" or "cephem" refers to a beta-lactam antibiotic comprising a 3,6-dihydro-2H-1,3-thiazine ring.

The term "carbapenem" refers to a beta-lactam antibiotic comprising a 2,3-dihydro-1H-pyrrole ring.

The term "penem" refers to a beta-lactam antibiotic comprising a 2,3-dihydrothiazole ring.

The term "monobactam" refers to a beta-lactam antibiotic comprising a beta-lactam ring not fused to any other ring.

Non-limiting examples of beta-lactam antibiotics may be selected from the group comprising benzylpenicillin, phenoxymethylpenicillin, methicillin, oxacillin, nafcillin, cloxacillin, dicloxacillin, flucloxacillin, mezlocillin, piperacillin, ticarcillin, temocillin, amoxicillin, ampicillin, azlocillin, carbenicillin, cephalexin, cephalothin, cefadroxil, cefprozil, cefdinir, cefditoren, ceftibuten, cefoperazone, ceftizoxime, ceftobiprole, cefaclor, cefuroxime, cefamandole, cefotetan, cefoxitin, ceftaroline, ceftriaxone, cefotaxime, cefpodoxime, cefixime, ceftazidime, imipenem, meropenem, ertapenem, faropenem, doripenem, aztreonam, tigemonam, nocardicin A, or combination thereof, or may be selected from any of these beta-lactam antibiotics in association with an inhibitor of beta-lactamase(s) such as, but not limited to clavulanic acid, tazobactam, or sulbactam, or in association with another molecule capable of protecting the beta-lactam antibiotic from degradation such as for example cilastatin for protecting imipenem.

In a first aspect, the present invention encompasses a method for measuring a free beta-lactam antibiotic in a biological sample, comprising the steps of:
(a) providing at least one class C beta-lactamase, a functional fragment or a variant thereof;
(b) providing at least one biological sample;
(c) contacting said at least one class C beta-lactamase with said at least one biological sample; and
(d) measuring said free beta-lactam antibiotic in said at least one biological sample.

Preferably, the present invention encompasses a method for determining the concentration of at least one free beta-lactam antibiotic in a biological sample, comprising the steps of:
(a) providing at least one class C beta-lactamase, a functional fragment or a variant thereof;
(b) providing at least one biological sample;
(c) contacting said at least one class C beta-lactamase with said at least one biological sample; and
(d) determining the concentration of said at least one free beta-lactam antibiotic in said at least one biological sample.

The biological sample can be derived from a biological origin, such as from a mammal, for instance from a human or animal. Preferably, the biological sample is derived from human origin.

The biological sample of interest for the measurement of beta-lactam antibiotic can be a biological fluid or a non-fluid biological sample. It should be understood by the skilled man that sample preparation before or during the present method can release the beta-lactam antibiotic for instance from a non-fluid biological sample. Hence, the present method can comprise the step of releasing the beta-lactam antibiotic from a non-fluid biological sample such as for instance a stool specimen.

Preferably, the biological sample is a biological fluid. The biological fluid can be selected from the group comprising serum, blood, urine, interstitial fluid, saliva, tears, exudates, fluid collected from deep tissues, fluid collected from subcutaneous tissues and other human fluids susceptible of containing beta-lactam antibiotic. Preferably, the biological sample is serum, blood, urine, or interstitial fluid, more preferably serum.

The biological sample of interest for the measurement of beta-lactam antibiotic can further be any biological fluid that can be processed through microdialysis.

Preferably, said sample is a microdialysate from a subject receiving an antibiotherapy.

The present method is particularly useful, for measuring the concentration and/or monitoring one or more beta-lactam antibiotics in the treatment of an infection caused by Gram positive or Gram negative micro-organisms in a subject in need thereof.

The present method is based on the interaction between a beta-lactam antibiotic and a class C beta-lactamase. The inventors have found that it is advantageous to use a class C beta-lactamase in a method for the measurement of a beta-lactam antibiotic in a biological sample, because it allows online and real-time monitoring of beta-lactam antibiotics in a biological sample such as in serum.

The class C beta-lactamase when contacted with a beta-lactam antibiotic, features kinetic parameters such that the hydrolysis rate of the beta-lactam antibiotic/class C beta-lactamase complex is rate limiting for the enzymatic reaction. In some embodiments, the residence time of a beta-lactam antibiotic into the class C beta-lactamase enzyme cavity is below 10 min, such as below 7 min, such as below 5 min.

The inventors have surprisingly shown that the hydrolysis rate of the beta-lactam antibiotic/class C beta-lactamase complex (acyl-enzyme complex) can be slow enough to allow the measurement of this complex for instance by spectroscopic methods, but rapid enough to allow the self-regeneration of the active enzyme which is advantageous to perform successive assays. The method of the present invention advantageously can make use of these features of the interaction between beta-lactam antibiotic and the class C beta-lactamase in order to allow the online and automated monitoring of beta-lactam antibiotics and can allow self-regeneration of said class C beta-lactamase.

As illustrated in the example section, class C beta-lactamases exhibit particular kinetic features which allow determining the concentration of beta-lactam antibiotics in a biological sample. The hydrolysis rate of the beta-lactam antibiotic/class C beta-lactamase complex (acyl-enzyme complex) can be slow enough to allow the measurement of this complex for instance by spectroscopic methods. This is in contrast with class A, class B, or class D beta-lactamases.

The method of the present invention can make use of the kinetic features of class C beta-lactamases to allow the determination of the concentration of a large variety of beta-lactam antibiotics as illustrated in the example section.

The term "self-regeneration", as used in the context of the present invention, refers to the capacity of the class C beta-lactamase to repeatedly perform its function i.e. bind, process and release a beta-lactam antibiotic.

According to the invention, the present method comprises the step of contacting at least one class C beta-lactamase with at least one biological sample.

In an embodiment, the present method comprises prior to the step of contacting at least one class C beta-lactamase with at least one biological sample, the step of contacting at least one class C beta-lactamase with at least one reporter substrate.

In this embodiment, the present method for measuring and/or quantifying and/or determining the concentration of a free beta-lactam antibiotic in a biological sample, comprises the steps of:
(a) providing at least one class C beta-lactamase, a functional fragment or variant thereof;
(b) providing at least one biological sample;
(b') contacting said biological sample with a reporter substrate;
(c') contacting said at least one class C beta-lactamase with said at least one biological sample comprising the reporter substrate; and
(d) measuring said free beta-lactam antibiotic in said at least one biological sample.

Using a reporter substrate, the present method advantageously allows the online and real-time measurement of beta-lactam antibiotics in biological samples. Furthermore, the reporter substrate provides a method which is particularly useful for automated measurement and/or quantification of beta-lactam antibiotics in biological fluids.

In an embodiment, the reporter substrate is a chromogenic substrate. In an embodiment, the reporter substrate comprises a beta-lactam ring. The reporter substrate can be a chromogenic substrate such as but not limited to the compound CENTA, as shown in Formula (IIa) or nitrocefin, as shown in Formula (IIb).

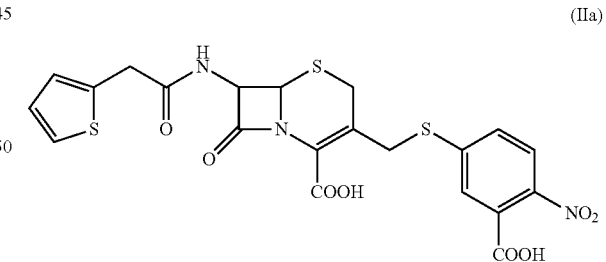

(IIa)

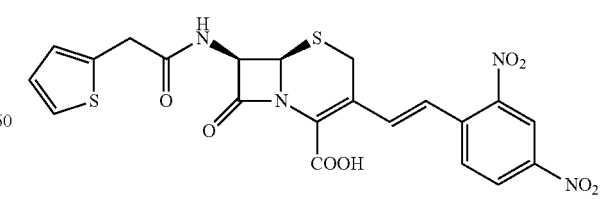

(IIb)

The reporter substrate can also be a fluorescent substrate. Non-limiting examples of suitable fluorescent reporter substrates include commercially available fluorescent substrates such as CCF2 fluorescent substrate of Invitrogen (San Diego, Calif.) or Fluorocillin™ Green beta-lactamase substrate of Molecular Probes, Invitrogen.

In some embodiments, the present method for measuring a free beta-lactam antibiotic in a biological sample can comprise the steps of contacting the biological sample to be tested with a chromogenic or fluorescent compound, and with the class C beta-lactamase, and measuring the amount of color or fluorescence developed in said biological sample in comparison with a standard, thereby measuring the concentration of antibiotic in said biological sample. The standard may represent a known amount or quantity of a beta-lactam antibiotic.

Preferably, the method comprises the steps of contacting the biological sample to be tested with a chromogenic compound, and the class C beta-lactamase, and measuring the amount of color developed in said biological sample in comparison with a standard, thereby measuring the concentration of antibiotic in said biological sample.

In an embodiment, the concentration of beta-lactam antibiotic is a relative concentration. In a preferred embodiment, the concentration of beta-lactam antibiotic is an absolute concentration. Advantageously, as illustrated in the example section, the methods embodying the principles of the present invention allow the determination of absolute concentrations of one or more beta-lactam antibiotics in a biological sample.

The recitation "determining the relative concentration" of a substance in a sample refers to the qualitative determination of the substance in the sample, i.e., determining whether the substance is present or absent in the sample.

The recitation "determining the absolute concentration" of a substance in a sample refers to the quantitative determination of the substance in the sample, i.e., determining the amount of the substance per volume of the sample. The determination of the absolute concentration of a beta-lactam antibiotic in a sample may be performed by comparison with one or more standards of known concentration.

Without being bound to a theory, this embodiment of the present method is based on the competition between the reporter substrate, acting as 'a substrate' and the beta-lactam antibiotic in the biological sample, acting as 'an inhibitor substrate' towards the catalytic site of the class C beta-lactamase. In the absence of beta-lactam antibiotic, the class C beta-lactamase hydrolyses more rapidly the reporter substrate and this reaction produces a signal. In the presence of a beta-lactam antibiotic, the class C beta-lactamase is no more available and thus unable to hydrolyze its reporter substrate. Accordingly, the higher the concentration of beta-lactam antibiotic, the lower the signal. The signal is thus inversely proportional to the beta-lactam antibiotic concentration present in the biological sample. The signal can be a color or fluorescence which can be measured with spectroscopy, such as ultraviolet-visible (UV-VIS) spectroscopy or fluorescence spectroscopy.

In a preferred embodiment, the reporter substrate is a chromogenic substrate, for instance CENTA or nitrocefin. In this embodiment, the present method can be considered as a colorimetric assay. The term "colorimetric assay", as used herein, refers to a method for measuring a free beta-lactam antibiotic in a biological sample, wherein the free beta-lactam antibiotic can be measured by ultraviolet-visible (UV-VIS) spectroscopy or fluorescence spectroscopy. Hence, in the present method, the free beta-lactam antibiotic can be measured by spectroscopy, preferably by Ultraviolet-visible (UV-VIS) spectroscopy; fluorescence spectroscopy; fluorescence resonance energy transfer (FRET) spectroscopy; or by Fourier Transform Infrared (FTIR) spectroscopy; or by plasmon resonance; or by surface sensitive wave based technique such as quartz crystal microbalance (QCM).

In an embodiment, the class C beta-lactamase can be immobilized. The class C beta-lactamase can be immobilized using methods such as impregnated on an inert material that can be glass fibers or polyester or any other material physically and chemically inert and with sufficient porosity and wettability to allow movement of the liquid biological sample and to allow the class C beta-lactamase to rehydrate easily and completely when the liquid biological sample reaches the enzyme. The reporter substrate such as a chromogenic substrate can also be immobilized. When the liquid biological sample is in contact with at least one rehydrated class C beta-lactamase and a reporter substrate such as a chromogenic substrate, the signal such as color development will depend on the concentration of the beta-lactam antibiotics in the biological sample. In a further embodiment, the class C beta-lactamase and/or the reporter substrate can be immobilized on a test strip.

As used herein, the term "beta-lactamase" refers to a class of proteins, in particular to a class of enzymes (EC 3.5.2.6) which are able to open a beta-lactam ring.

As used herein, the term "class C", "AmpC" or "group 1" beta-lactamase, refers to a class of beta-lactamases which (i) in the Ambler primary structural classification belong to the molecular class C (Ambler, Philos. Trans. R. Soc. Lond. B. Biol. Sci., 1980, 289: 321-31) and (ii) in the functional classification of Bush et al. belong to group 1 (Antimicrob. Agents Chemother., 1995, 39, 1211-33). In an embodiment, the class C beta-lactamases for use in the present method can be cephalosporinases poorly inhibited or not inhibited by clavulanic acid.

The class C beta-lactamase may also encompass functional fragments thereof. The term "functional fragment", as used herein, refers to a fragment of a class C beta-lactamase which is able to open a beta-lactam ring. The term "fragment" of a protein refers to an N-terminally, and/or C-terminally, and/or internal deleted or truncated form of said protein. Without limitation, a fragment of said class C beta-lactamase for use in the present invention may represent at least about 5%, or at least about 10%, e.g., $\geq 20\%$, $\geq 30\%$ or $\geq 40\%$, such as preferably $\geq 50\%$, e.g., $\geq 60\%$, $\geq 70\%$ or $\geq 80\%$, or more preferably $\geq 90\%$ or $\geq 95\%$ of the amino acid sequence of said class C beta-lactamase.

The class C beta-lactamase may also encompass functional variants or isoforms thereof. The term "functional variant or isoform", as used herein, refers to a variant or isoform of a class C beta-lactamase which is able to open a beta-lactam ring. Any such functional variants or isoforms of said class C beta-lactamase are intended herein. Without limitation, a variant or isoform of said class C beta-lactamase may have at least about 10%, e.g., at least 20%, at least 30% or at least 40%, such as preferably at least 50%, e.g., at least 60%, at least 70% or at least 80%, or more preferably at least 90% or at least 95% of sequence identity with the amino acid sequence of said wild type class C beta-lactamase. A variant of said class C beta-lactamase may also encompass a single or multiple mutated mutant, in which a single mutated mutant contains only one amino acid substitution and a multiple mutated mutant contains more than one amino acid substitution in the amino acid sequence of said wild type class C beta-lactamase.

The class C beta-lactamase can be found in or derived from nature. The class C beta-lactamase can also be produced by recombinant or synthetic means.

The class C beta-lactamase can be encoded by a nucleic acid sequence (i) isolated from a bacterium or (ii) encoded on the chromosome of a bacterium, wherein said bacterium is a Gram-negative bacterium, preferably a Gram-negative bacterium selected from a bacterium of the *Citrobacter*, *Enterobacter* or *Serratia* species. In a particular embodiment, said bacterium can be a *Citrobacter freundii*, *Enterobacter cloacae* P99, *Enterobacter cloacae* 908R, *Escherichia coli* K12, *Serratia marcescens* or *Pseudomonas aeruginosa*.

In a further embodiment, the class C beta-lactamase for use in the present invention can be encoded from a plasmid, wherein said plasmid is selected from the group of plasmids carrying genes encoding for one or more of ACT-1, MIR-1, CMY-1 and CMY-2 class C beta-lactamases.

Suitable non-limiting examples of class C beta-lactamase, with their catalytic constants are listed in Tables A and B. Suitable class C beta-lactamases can have low kcat and Km for the penicillins antibiotics comparatively to the class A beta-lactamases. Beta-lactams with low Km and kcat can be easily quantified with the class C beta-lactamase by the present method.

having primary amino acid sequence as annotated under Uniprot/Swissprot accession number P05364 or X07274 (www.uniprot.org/uniprot/).

In certain embodiments of the present method, the class C beta-lactamase may be a recombinant class C beta-lactamase of *Enterobacter cloacae* P99 wherein the N-terminal signal peptide has been replaced by two amino acids namely methionine and alanine (MA). In certain embodiments, the class C beta-lactamase may be a recombinant class C beta-lactamase of *Enterobacter cloacae* P99 wherein the first 21 amino acids (MMRKSLCCALLLGISCSALAT) have been replaced by two amino acids (MA). In certain embodiments, the class C beta-lactamase is a recombinant class C beta-lactamase of *Enterobacter cloacae* P99 encoded by a nucleic acid sequence of SEQ ID NO. 5 (FIG. 5). In certain embodiments, the class C beta-lactamase comprises the amino acid sequence of SEQ ID NO. 6 (FIG. 6).

In a further preferred embodiment, the class C beta-lactamase used in the present method is a variant of *Enterobacter cloacae* P99 class C beta-lactamase which has been modified so as to have the alanine 266 replaced by cysteine.

TABLE A

| | | Penicillins | | Cephalosporins | | |
|---|---|---|---|---|---|---|
| Class | kcat (s$^{-1}$) | Benzylpenicillin | Ampicillin | Nitrocefin | Cephaloridine | Cefuroxime |
| C | *Enterobacter cloacae* P99 | 14 | 0.74 | 780 | 700 | 0.05 |
| | *Enterobacter cloacae* 908R | 18 | 0.53 | 780 | 600 | 0.05 |
| | *Citrobacter freundii* | 31 | 6.5 | 330 | 700 | 0.04 |
| | *Escherichia coli* K12 | 45 | 4.2 | 490 | 130 | 0.15 |
| | *Serratia marcescens* | 75 | 0.46 | 1240 | 1100 | 0.8 |
| | *Pseudomonas aeruginosa* | 76 | 4.4 | 742 | 110 | 0.05 |

TABLE B

| | | Penicillins | | Cephalosporins | | |
|---|---|---|---|---|---|---|
| Class | Km (uM) | Benzylpenicillin | Ampicillin | Nitrocefin | Cephaloridine | Cefuroxime |
| C | *Enterobacter cloacae* P99 | 0.6 | 0.4 | 25 | 70 | 0.016 |
| | *Enterobacter cloacae* 908R | 0.5 | 0.4 | 23 | 75 | 0.016 |
| | *Citrobacter freundii* | 0.4 | 0.2 | 12 | 35 | 0.020 |
| | *Escherichia coli* K12 | 4.4 | 3.5 | 500 | 170 | 0.150 |
| | *Serratia marcescens* | 1.7 | 0.01 | 40 | 275 | 0.6 |
| | *Pseudomonas aeruginosa* | 1.7 | 0.5 | 27 | 20 | 0.02 |

Preferred class C beta-lactamase can be selected from the group comprising class C beta-lactamase of *Enterobacter cloacae* P99, *Enterobacter cloacae* 908R, *Citrobacter freundii*, *Escherichia coli* K12, *Serratia marcescens* or *Pseudomonas aeruginosa*, or a functional fragment or variant thereof.

In a preferred embodiment, the class C beta-lactamase used in the present method is the class C beta-lactamase of *Enterobacter cloacae* P99, also referred as P99 beta-lactamase. Preferably, the class C beta-lactamase of *Enterobacter cloacae* P99 comprises at its N-terminus a signal peptide of 21 amino acids. In certain embodiments, the class C beta-lactamase of *Enterobacter cloacae* P99 is encoded by a nucleic acid sequence of SEQ ID NO. 9 (FIG. 11). In certain embodiments, the class C beta-lactamase of *Enterobacter cloacae* P99 comprises the amino acid sequence of SEQ ID NO. 10 (FIG. 12).

Exemplary class C beta-lactamase of *Enterobacter cloacae* P99 includes, without limitation, class C beta-lactamase In certain embodiments, the class C beta-lactamase used is encoded by a nucleic acid sequence of SEQ ID NO. 11 (FIG. 13). In certain embodiments, the class C beta-lactamase comprises the amino acid sequence of SEQ ID NO. 12 (FIG. 14).

In certain embodiments, the class C beta-lactamase may be a variant of class C beta-lactamase of *Enterobacter cloacae* P99 wherein the first 21 amino acids (MMRKSLC-CALLLGISCSALAT) have been replaced by two amino acids (MA) and wherein 'wild type' alanine 266, which is renumbered as alanine 247, has been replaced by cysteine. In certain embodiments, the class C beta-lactamase is a variant of class C beta-lactamase of *Enterobacter cloacae* P99 encoded by a nucleic acid sequence of SEQ ID NO. 7 (FIG. 7). In certain embodiments, the class C beta-lactamase comprises the amino acid sequence of SEQ ID NO. 8 (FIG. 8).

In some embodiment, said class C beta-lactamase used in the present method is a variant of *Enterobacter cloacae* P99 beta-lactamase, said variant comprising an amino acid sequence selected from:

(a) an amino acid sequence encoded by a nucleic acid sequence of SEQ ID No. 7 or SEQ ID No 11, or
(b) an amino acid sequence of SEQ ID No. 8 or SEQ ID No. 12.

The present method is also particularly suitable for determining the individual concentration of two or more free beta-lactam antibiotics in a biological sample.

When two or more beta-lactam antibiotics are present in the sample, a separation step for separating the different beta-lactam antibiotics can be used, prior to contacting the sample with the beta-lactamase. In an embodiment, the antibiotics are separated using chromatography techniques.

The present method is also particularly suitable for determining the individual concentration of two or more free beta-lactam antibiotics in a biological sample using at least one class C beta-lactamase, and at least one other beta-lactamase.

In certain embodiments, the method for determining the individual concentration of two or more free beta-lactam antibiotics in a biological sample may comprise the steps of:
(a) providing a class C beta-lactamase, a functional fragment or variant thereof;
(a') providing a class A, class B, or class D beta-lactamase, or providing a second class C beta-lactamase which is different from the class C beta-lactamase provided in step (a);
(b) providing at least one biological sample;
(c) contacting said class C beta-lactamase with said at least one biological sample; and
(c') contacting said class A, class B, or class D beta-lactamase with said at least one biological sample, or contacting said second class C beta-lactamase with said at least one biological sample; and
(d) determining the concentration of said two or more free beta-lactam antibiotics in said at least one biological sample.

In a preferred embodiment, the concentration of said two or more beta-lactam antibiotics in at least one biological sample is determined with a class C beta-lactamase of *Enterobacter cloacae* P99, a functional fragment or variant thereof, and a second beta-lactamase different from said class C beta-lactamase of *Enterobacter cloacae* P99, functional fragment or variant thereof. Using the class C beta-lactamase advantageously allows the determination of a very large variety of beta-lactam antibiotics compared with the other classes of beta-lactamases namely class A, class B, or class D beta-lactamases.

The method may comprise the step of determining the reaction rate of the class C beta-lactamase in a biological sample without beta-lactam antibiotic and in biological samples comprising known concentrations of the beta-lactam antibiotic of which the concentration is to be determined (standards). The method may further comprise the step of contacting said class C beta-lactamase with said at least one biological sample and determining the residual reaction rate of the class C beta-lactamase in the biological sample. These steps may be repeated for the class A, class B, or class D beta-lactamase or for the second class C beta-lactamase. The concentration of two or more beta-lactam antibiotics in a biological sample may be determined by calculating the concentrations from the residual reaction rates of two or more beta-lactamase enzymes, i.e., at least a class C beta-lactamase and a class A, class B, or class D beta-lactamase or a second class C beta-lactamase.

The concentration of two beta-lactam antibiotics in a biological sample may be determined as described herein below.

Generally, in competitive inhibition, the kinetic data can be linearized by reporting the inverse of the reaction rate in function of the concentration of inhibitors such as beta-lactam antibiotics:

$$Y = aC + b \quad (\text{eq.1})$$

wherein $$Y = \frac{v_{0max}}{v_0} - 1, \quad (\text{eq. 2})$$

$v_0$ is the residual reaction rate ($\Delta A^{482}$/min), $v_{0\ max}$ is the reaction rate ($\Delta Abs^{482}$/min) without inhibitors.

When two or more competitive inhibitors are present:

$$Y = a_1 C_1 + b_1 + a_2 C_2 + b_2 + a_n C_n + b_n \quad (\text{eq.3})$$

wherein $C_{1, 2, \ldots, n}$ are the concentrations of inhibitor 1, 2, . . . and n respectively.

To quantify the individual concentration in a mixture of two inhibitors, two enzymes were used to solve the equations, for example P99 and class D oxa-29 beta-lactamase:

From (eq.3):

$$Y_{P99} = a_1 C_A + b_1 + a_2 C_C + b_2 \quad (\text{eq.4})$$

wherein $C_A$ and $C_C$ are the concentrations to be determined of beta-lactam antibiotic A and beta-lactam antibiotic C respectively.

Rearranging (eq.4) to solve:

$$C_A = \frac{Y_{P99} - a_2 C_C - b_2 - b_1}{a_1} \quad (\text{eq. 4.1})$$

Rearranging (eq.4) to solve:

$$C_C = \frac{Y_{P99} - a_1 C_A - b_1 - b_2}{a_2} \quad (\text{eq. 4.2})$$

From (eq.3):

$$Y_{Oxa} = a_3 C_A + b_3 + a_4 C_C + b_4 \quad (\text{eq.5})$$

Rearranging (eq.5) to solve:

$$C_A = \frac{Y_{Oxa} - a_4 C_C - b_4 - b_3}{a_3} \quad (\text{eq. 5.1})$$

Rearranging (eq.5) to solve:

$$C_C = \frac{Y_{Oxa} - a_3 C_A - b_3 - b_4}{a_4} \quad (\text{eq. 5.2})$$

From equations (eq.4.1) and (eq.5.1), the concentration of beta-lactam antibiotic C($C_C$) can be determined:

$$C_C = \frac{a_1 Y_{Oxa} - a_3 Y_{P99} - a_1 b_4 - a_1 b_3 + a_3 b_2 + a_3 b_1}{a_1 a_4 - a_2 a_3}$$

From equations (eq.4.2) and (eq.5.2), the concentration of beta-lactam antibiotic A ($C_A$) can be determined:

$$C_A = \frac{a_2 Y_{Oxa} - a_4 Y_{P99} - a_2 b_3 - a_2 b_4 + a_4 b_1 + a_4 b_2}{a_2 a_3 - a_1 a_4}.$$

The present invention also encompasses in a further aspect, a class C beta-lactamase which is a variant of the *Enterobacter cloacae* P99 class C beta-lactamase which has been modified so as to have the alanine 266 replaced by a cysteine, also referred to herein as P99A266C. In particular, the invention encompasses a variant of *Enterobacter cloacae* P99 beta-lactamase wherein the alanine at position 266 of P99 lactamase is substituted by a cysteine. For example, the invention encompasses a variant of *Enterobacter cloacae* P99 beta-lactamase encoded by a nucleic acid sequence of SEQ ID NO. 11. For example, the invention encompasses a variant of *Enterobacter cloacae* P99 beta-lactamase comprising an amino acid sequence having SEQ ID NO. 12.

The variant of *Enterobacter cloacae* P99 beta-lactamase can comprise an amino acid sequence selected from: (a) an amino acid sequence encoded by a nucleic acid sequence of SEQ ID No. 11, or (b) an amino acid sequence SEQ ID No. 12.

In a further aspect, the present invention also encompasses a class C beta-lactamase which is a variant of the *Enterobacter cloacae* P99 class C beta-lactamase which has been modified so as to have the first 21 amino acids (MMRKSLCCALLLGISCSALAT) replaced by two amino acids (MA) and to have the alanine 247, i.e., renumbered alanine 266, replaced by a cysteine. For example, the invention encompasses a variant of *Enterobacter cloacae* P99 beta-lactamase encoded by a nucleic acid sequence of SEQ ID NO. 7. For example, the invention encompasses a variant of *Enterobacter cloacae* P99 beta-lactamase comprising an amino acid sequence of SEQ ID NO. 8.

The variant of *Enterobacter cloacae* P99 beta-lactamase can comprise an amino acid sequence selected from: (a) an amino acid sequence encoded by a nucleic acid sequence of SEQ ID No. 7, or (b) an amino acid sequence SEQ ID No. 8.

The recitations "P99A266C signal peptide variant", or "P99A247C" may be used interchangeably herein. The term "P99A247C variant" as used herein refers to a variant of the *Enterobacter cloacae* P99 class C beta-lactamase which has been modified so as to have the first 21 amino acids (MMRKSLCCALLLGISCSALAT) replaced by two amino acids (MA) and to have the alanine 247 replaced by a cysteine.

The class C beta-lactamase P99A266C or P99A247C allows the measurement of a free beta-lactam antibiotic in a biological sample. The class C beta-lactamase P99A266C or P99A247C advantageously allows to immobilize the class C beta-lactamase for example to be used in a colorimetric assay as defined herein. The class C beta-lactamase P99A266C or P99A247C further allows coupling of the class C beta-lactamase with a device. The cysteine present in P99A266C or P99A247C advantageously allows to covalently couple the class C beta-lactamase with an organic molecule or a multifunctional arm-spacer of the device, both as defined herein. The thiol group present in said cysteine at position 266 in P99A266C or at position 247 in P99A247C advantageously is available in the opposite direction of the active site of the class C beta-lactamase, thereby avoiding to disturb the enzymatic activity of the class C beta-lactamase.

Indeed, the present inventors have shown that the mutation or replacement of alanine at position 266 to cysteine in the class C beta-lactamase P99 did not affect the enzyme activity.

In an embodiment, the P99A266C beta-lactamase is produced by recombinant means. For instance, P99A266C can be produced with standard cloning and expression techniques, both known in the art. In short, the wild type class C beta-lactamase of *Enterobacter cloacae* P99 has been PCR amplified and cloned in a cloning vector and subsequently transferred to an expression vector. P99A266C can be obtained by site-directed mutagenesis, for example using specific primers, comprising the mutation for substituting the alanine 266 in wild type class C beta-lactamase of *Enterobacter cloacae* P99 to a cysteine.

In view of the above, it shall be appreciated the invention also encompasses aspects relating to recombinant means and reagents useful for obtaining a recombinant microorganism, methods for obtaining a recombinant microorganism using such recombinant means and reagents, methods for expressing the desired protein i.e. P99A266C or P99A247C in a recombinant microorganism, as well as to the expressed proteins and combinations thereof per se and methods for preparation thereof.

Accordingly, further encompassed herein is a recombinant nucleic acid encoding a variant of *Enterobacter cloacae* P99 beta-lactamase, comprising a nucleic acid sequence selected from: (a) the nucleic acid sequence of SEQ ID No. 7 or SEQ ID NO. 11, or (b) the nucleic acid sequence encoding a amino acid sequence of SEQ ID No. 8 or SEQ ID NO. 12.

Also disclosed are vectors, such as for instance cloning vectors, shuttle vectors and/or expression vectors, comprising one or more of the recombinant nucleic acids as disclosed above.

Further embodiments provide host microorganisms of interest transformed with one or more of the recombinant nucleic acids or with a vector as described above. In an embodiment, the microorganism may be a bacterium, for instance a bacterium such as *Escherichia coli*. Such bacteria are particularly suitable for overproduction of recombinant proteins, for example for purposes of purification.

According to an embodiment, the present method comprises the step of contacting at least one class C beta-lactamase with at least one biological sample. In an embodiment, said at least one class C beta-lactamase is grafted on at least one surface of a device, wherein said at least one surface is at least one chemically activated surface of a device, or is at least one metal plated surface of a device.

According to this embodiment, the present method comprises the steps of: (a) providing at least one class C beta-lactamase, a functional fragment or variant thereof, wherein said at least one class C beta-lactamase is grafted on at least one chemically activated or metal plated surface of a device; (b) providing at least one biological sample; (c) contacting said at least one class C beta-lactamase with said at least one biological sample; and (d) measuring and/or quantifying said free beta-lactam antibiotic in said at least one biological sample.

Hence, the present method can use a device on which a class C beta-lactamase is grafted. The terms "grafted", "coupled" or "bound", as used herein, refer to the covalent incorporation of a class C beta-lactamase, a functional fragment or variant thereof on a device.

The device is also referred herein as "biosensor". By the term "biosensor" it is meant a device based on the specific recognition of an analyte of interest by a target such as a biological component, for example a receptor, an antibody, an enzyme, a membrane, a cell or cell containing media, a molecule and the subsequent transformation of this interaction into an electrical, optical, or other signal. In an embodiment, the term "biosensor" or "beta-lactam antibiotic biosensor" particularly refers to a device provided to specifically recognize a beta-lactam antibiotic using a class C beta-lactamase grafted on said biosensor.

Using a device on which a class C beta-lactamase is grafted, the present method is particularly useful for online and real-time measurement and/or quantification of beta-lactam antibiotics in biological samples. Using a device on which a class C beta-lactamase is grafted, the present method is particularly useful for automated measurement and/or quantification of beta-lactam antibiotics in biological samples, such as for example serum. Using a device on which a class C beta-lactamase is grafted, the present method allows self-regeneration of the device or provides the device with a self-regenerative capacity, i.e. the capacity to be re-used without the need to regenerate the device. The self-regenerative capacity of the device used in the present method allows monitoring and adjustment of beta-lactam antibiotics in a biological sample in an efficient and hence economical way.

Preferably, the class C beta lactamase is selected from the group comprising class C beta-lactamase of *Enterobacter cloacae* P99, *Enterobacter cloacae* 908R, *Citrobacter freundii*, *Escherichia coli* K12, *Serratia marcescens* or *Pseudomonas aeruginosa*, or a functional fragment or variant thereof, preferably said class C beta-lactamase is C beta-lactamase of *Enterobacter cloacae* P99, yet more preferably said class C beta-lactamase is a variant of *Enterobacter cloacae* P99 beta-lactamase wherein the alanine at position 266 is substituted by a cysteine.

In an embodiment, the device used in the present method comprises an attenuated total internal reflection element, transparent in the infrared. In this embodiment, the beta-lactam antibiotic is measured with surface sensitive optical methods. In this embodiment, the free beta-lactam antibiotic concentration is measured by Fourier Transform Infrared (FTIR)-ATR spectroscopy. FTIR-ATR spectroscopy is a rapid, selective and efficient label-free analytical method.

According to an embodiment of the invention, the device comprises an attenuated total internal reflection element (ATR), transparent in the infrared of which at least one surface is chemically activated and covalently grafted with a class C beta-lactamase. The ATR configuration allows the study of analytes such as biological components and molecules or proteins, on surfaces in contact with a sample.

In an embodiment, the present method comprises the steps of: (a) providing at least one class C beta-lactamase, a functional fragment or variant thereof, wherein said at least one class C beta-lactamase is grafted on at least one chemically activated surface of an attenuated total internal reflection element, transparent in the infrared; (b) providing at least one biological sample; (c) contacting said at least one class C beta-lactamase with said at least one biological sample; and (d) measuring and/or quantifying said free beta-lactam antibiotic in said at least one biological sample.

In another embodiment, the present method comprises the steps of: (a) providing at least one class C beta-lactamase, a functional fragment or variant thereof, wherein said at least one class C beta-lactamase is grafted on at least one metal plated surface of an attenuated total internal reflection element, transparent in the infrared; (b) providing at least one biological sample; (c) contacting said at least one class C beta-lactamase with said at least one biological sample; and (d) measuring and/or quantifying said free beta-lactam antibiotic in said at least one biological sample.

A purposely modified ATR element can be provided to study beta-lactam antibiotic/class C beta-lactamase interactions occurring at the solvent ATR element interface, particularly, at the water-containing media-ATR element interface, by using attenuated total internal reflection (ATR) infrared (IR) spectroscopy, preferably Fourier transform infrared spectroscopy (FTIR). In an embodiment, using an ATR element of which at least one surface is chemically activated and covalently grafted with a class C beta-lactamase, the method of the present invention allows automated and online monitoring and adjustment of beta-lactam antibiotics.

In an embodiment, when the class C beta-lactamase is coupled on an ATR element, the residence time of a beta-lactam antibiotic into the class C beta-lactamase enzyme cavity may be estimated at about 100 seconds. Preferably, when using an ATR element, the residence time of the beta-lactam antibiotic into the class C beta-lactamase enzyme cavity can be less than 10 min thereby allowing recycling the sensor and starting a new measure.

In an embodiment, the device used for measuring and/or quantifying beta-lactam antibiotic, is preferably based on FTIR-ATR technology. Fourier transform Infrared (FTIR) spectroscopy is an extremely powerful analytical technique, particularly well adapted to the characterization of organic molecules and biological systems. Quantitative structural and conformational information can be recorded. Hence, a method is provided wherein the binding of free beta-lactam antibiotic to said class C beta-lactamase is monitored by FTIR-ATR spectroscopy.

In one embodiment, the ATR element is made of a material selected from the group consisting of silicon, germanium, ZnS, ZnSe, or diamond. Preferably, the ATR element is made of germanium or silicon and more preferably the ATR element is made of germanium.

In another embodiment, the ATR element can have any shape as long as it allows internal reflection of a radiation within said ATR element. Preferably, the ATR element is a crystal having a trapezoidal, hemi-cylindrical, rectangular or triangular polyhedral form, rectangular prism, or a triangular prism (prism with triangular basis). More preferably, the ATR element is a triangular prism with a right triangular basis (also called right-angled triangle or rectangled triangle). More preferably, the ATR element is a triangular prism with 45-45-90 triangle basis (right triangle with the two other angles at 45°).

In other embodiments, the device which can be used in the method can be a surface Plasmon resonance sensor such as the BIACORE/Surface Plasmon Resonance sensor.

In yet another embodiment, the device used in the method is a quartz crystal microbalance. In this embodiment, the beta-lactam antibiotic is measured with surface sensitive waveguide techniques.

As used herein "quartz crystal microbalance" (QCM) refers to a mass-sensing device. An electrical signal is sent through a quartz crystal, producing a vibration at a resonance frequency. Changes in frequency are related to changes in mass on the surface of the crystal.

In an embodiment, QCMs preferably function as biosensors. In an embodiment, class C beta-lactamase is associated with the QCM surface. Subsequent binding of the beta-lactam antibiotic results in a measurable change in the resonance frequency. In an embodiment, the class C beta-lactamase associated with the QCM provides beta-lactam antibiotic's recognition and self-regenerative capacity to the QCM.

In this embodiment, the present method for measuring and/or quantifying a free beta-lactam antibiotic in a biological sample, comprises the steps of: (a) providing at least one class C beta-lactamase, a functional fragment or variant thereof, wherein said at least one class C beta-lactamase is grafted on at least one chemically activated or metal plated surface of a quartz crystal microbalance; (b) providing at least one biological sample; (c) contacting said at least one class C beta-lactamase with said at least one biological sample; and (d) measuring and/or quantifying said free beta-lactam antibiotic in said at least one biological sample.

In an embodiment, the surface of the ATR element or the QCM can be coated or plated with metal films such as gold films. Preferably such metal films can have a thickness of 3 to 15 nm, such as 5 to 10 nm. Metals other than gold are e.g. Ag, Cu, Pt, Au/Pt, alloys, particularly gold comprising alloys, multilayers, particularly bilayers of metals such as gold on chromium or titanium. Such plated device can be produced by coating an ATR element or a QCM with a thin metal layer on at least one face. Such coating is performed by means of known methods for the preparation of thin metallic films, e.g. physical vapor deposition (PVD).

According to a further embodiment, the device comprises an ATR element or a gold-coated quartz crystal, of which at least one surface is chemically activated and covalently grafted with a class C beta-lactamase, a fragment or a variant thereof.

The surface can be activated by wet chemistry using oxidation/hydroxylation/reduction in an acid or alkaline environment. The activation results from the surface oxidation or hydroxylation by any available technique (physical or chemical), preferably by the wet-chemistry technique using a solution of an oxidant in acidic or basic media, such as $H_2O_2/H_2SO_4$, $H_2O_2$/TFA, $H_2O_2$/HF, $K_2Cr_2O_7/H_2SO_4$, oxone/$H_2SO_4$, $H_2O_2$/$NH_4OH$, or in organic media, such as an organic peracid, $Br_2$ in solution. The activation may also be carried out by dipping the crystals in sequences of solutions of an oxidant in acidic or basic media. Suitable solutions of an oxidant in acidic or basic media, are e.g. $H_2O_2/H_2SO_4$, $H_2O_2$/TFA, $H_2O_2$/HF, $K_2Cr_2O_7/H_2SO_4$, oxone/$H_2SO_4$, $H_2O_2$/$NH_4OH$, or e.g. in organic media, such as an organic peracid, $Br_2$ in a suitable solution, or a combination of these solutions in specific sequences, such as HF in water followed by $H_2O_2$ in water, which can be iterated for several times e.g. number of repetitions: 2, 3, 4, 5 . . . or $NH_4OH/H_2O_2$ in water followed by $HCl/H_2O_2$ in water e.g. number of repetitions: 1. The temperature can be comprised between $-15°$ C. and $+150°$ C. The duration of the treatment can be comprised between a few seconds to several hours.

In an embodiment, the class C beta-lactamase can be grafted on at least one activated or metal plated surface of the ATR element or on the gold-plated quartz crystal, via an organic molecule of Formula (III), (IV), (V), (VI), (VII), (VIII), (IX), (X), (XI) or (XII), $$HS-(CH_2-CH_2-O)_w-CH_3 \quad (III)$$

$$X^1{}_3Si-(CH_2)_q-NH-COO-(CH_2)_s-X^1 \quad (IV)$$

$$CH=CR^6 \quad (V)$$

$$CH_2=CHR^6 \quad (VI)$$

$$X^1{}_3Si-(CH_2)_q-(CF_2)_s-Y^1 \quad (VII)$$

$$X^1{}_2(R^3)Si-(CH_2)_q-(CF_2)_s-Y^1 \quad (VIII)$$

$$X^1(R^3)(R^4)Si-(CH_2)_q-(CF_2)_s-Y^1 \quad (IX)$$

$$X^1{}_3Si-(L^1)_n-NH-COO-(L^2-O)_m-L^3-X^1 \quad (X)$$

$$X^1{}_2(R^3)Si-(L^1)_n-NH-COO-(L^2-O)_m-L^3-X^1 \quad (XI)$$

$$X_1(R^3)R^4Si-(L^1)_n-NH-COO-(L^2-O)_m-L^3-X^1 \quad (XII)$$

wherein $X^1$ is halogen or $C_{1-6}$alkoxy; $Y^1$ is Me, $CF_3$, $CHF_2$, $CH_2F$, $CH=CH_2$, CN, CH=O, epoxy, halogen, SH, $NH_2$ or N-maleimide or N-succinimide derivative thereof, OH, N=C=O, N=C=S, $CO_2H$ or N-hydroxysuccinimide ester thereof; $R^3$ and $R^4$ are each independently $C_{1-6}$alkyl; $R^6$ is selected from $C_wH_{2w+1}$, $C_wF_{2w+1}$, or $-(CH_2)_u-(O-CH_2-CH_2)_p-OR^5$; wherein $R^5$ is selected from $C_{1-4}$alkyl, $C_{1-6}$alkylarylsulfoxide, heteroaryloxycarbonyl$C_{1-6}$alkyl,

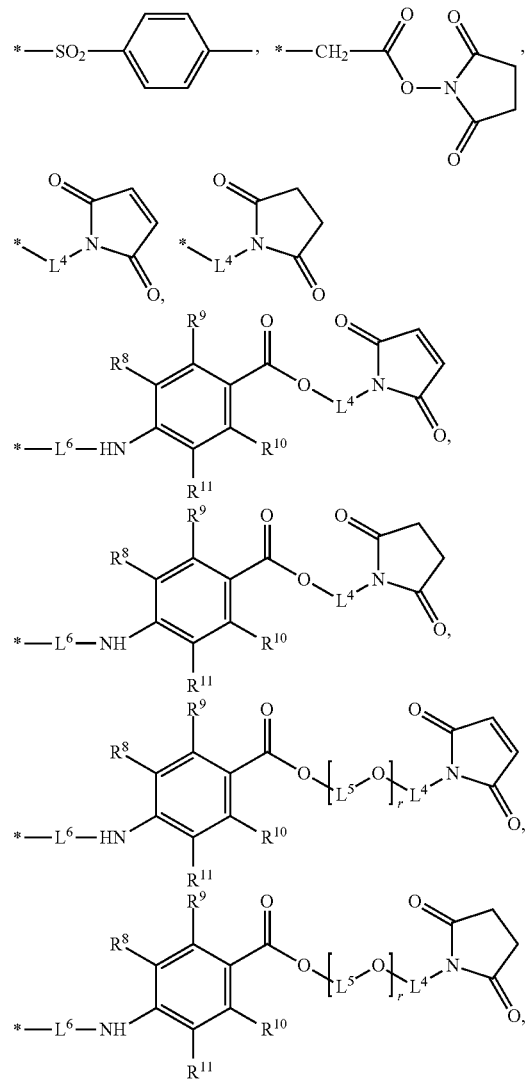

or mixture thereof; $L^1$ is $C_{1-6}$alkylene, optionally substituted by halogen; $L^2$ is $C_{1-6}$alkylene; $L^3$ is $C_{1-6}$alkylene, optionally substituted with $R^7$, wherein $R^7$ is

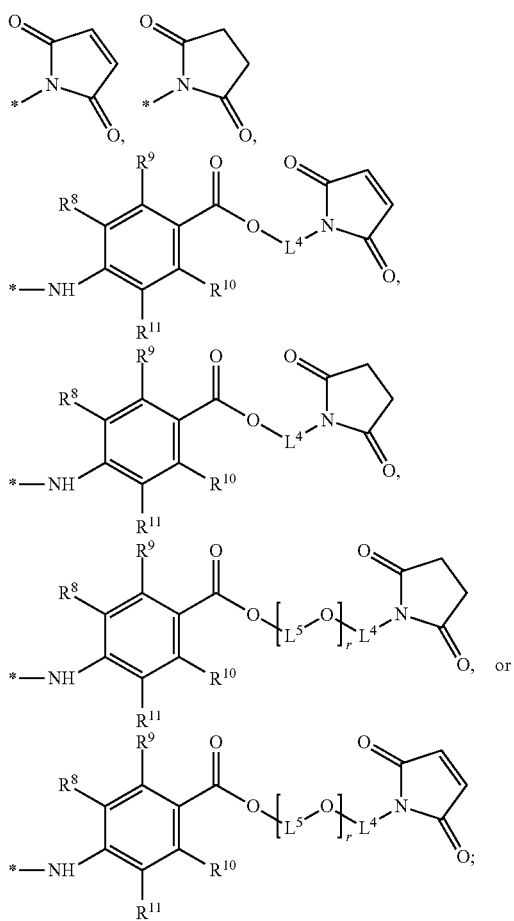

$L^4$ is $C_{1-20}$alkylene; $L^5$ is $C_{1-6}$alkylene; $L^6$ is $C_{1-6}$alkylene, optionally substituted with $C_{1-6}$alkoxy; each of $R^8$, $R^9$, $R^{19}$ and $R^{11}$ are independently selected from hydrogen, $C_{1-6}$alkyl, $C_{1-6}$alkoxy or halogen;

w is an integer selected from 3 to 50, for instance, w is 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50, q is an integer selected from 1 to 20, for instance, q is 1, 2, 3, 4, 5, 6, 7, 8, 9, 10, 11, 12, 13, 14, 15, 16, 17, 18, 19, or 20;

s is an integer selected from 0 to 20, for instance, s is 0, 1, 2, 3, 4, 5, 6, 7, 8, 9, 10, 11, 12, 13, 14, 15, 16, 17, 18, 19, or 20;

n is an integer selected from 1 to 10; for instance, n is 1, 2, 3, 4, 5, 6, 7, 8, 9, or 10;

m is an integer selected from 1 to 20; for instance, m is 1, 2, 3, 4, 5, 6, 7, 8, 9, 10, 11, 12, 13, 14, 15, 16, 17, 18, 19, or 20;

u is an integer selected from 0 to 20; for instance, u is 0, 1, 2, 3, 4, 5, 6, 7, 8, 9, 10, 11, 12, 13, 14, 15, 16, 17, 18, 19, or 20;

p is an integer selected from 3 to 20; for instance, p is 3, 4, 5, 6, 7, 8, 9, 10, 11, 12, 13, 14, 15, 16, 17, 18, 19, or 20;

r is an integer selected from 1 to 20, for instance, r is 1, 2, 3, 4, 5, 6, 7, 8, 9, 10, 11, 12, 13, 14, 15, 16, 17, 18, 19, or 20.

As used herein, the term "alkyl" by itself or as part of another substituent, refers to a straight or branched saturated hydrocarbon group joined by single carbon-carbon bonds having 1 to 10 carbon atoms, for example 1 to 8 carbon atoms, for example 1 to 6 carbon atoms or for example 1 to 4 carbon atoms. When a subscript is used herein following a carbon atom, the subscript refers to the number of carbon atoms that the named group may contain. Thus, for example, $C_{1-6}$alkyl means an alkyl of one to six carbon atoms. Examples of alkyl groups are methyl, ethyl, propyl, isopropyl, butyl, isobutyl, sec-butyl, tert-butyl, 2-methylbutyl, pentyl iso-amyl and its isomers, hexyl and its isomers, heptyl and its isomers and octyl and its isomers. Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene.

The term "aryl" as used herein by itself or as part of another group refers but is not limited to 5 to 14 carbon-atom homocyclic (i.e., hydrocarbon) monocyclic, bicyclic or tricyclic aromatic rings or ring systems containing 1 to 4 rings which are fused together or linked covalently, typically containing 5 to 10 atoms; at least one of which is aromatic. Where aryl groups as defined are divalent, i.e., with two single bonds for attachment to two other groups, they are termed "arylene" groups.

The term "$C_{1-6}$alkylcarbonyl" as used herein refers to a group of general formula $C_{1-6}$alkyl-CO, wherein $C_{1-6}$alkyl is as defined above.

The term "amino" refers to the group —$NH_2$.

The term "halo" or "halogen" as a group or part of a group is generic for fluoro, chloro, bromo or iodo.

The term "epoxy" as used herein refers to cyclic ether with only three ring atoms.

The term "$C_{1-6}$alkylarylsulfoxide" as used herein refers to a compound with a $C_{1-6}$alkyl moiety, an aryl moiety and a group of general formula —$SO_2$.

The term "heteroaryl" as used herein refers to a group of five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulfur and wherein an N atom may be in the form of an N-oxide.

The term "heteroaryloxycarbonyl$C_{1-6}$alkyl" as used herein refers to a group of general formula heteroaryl-O—C(O)—$C_{1-6}$alkyl group where R is a $C_{1-6}$alkyl is a group as previously described heteroaryl group as previously described.

The term "$C_{1-6}$alkoxy" as used herein refers to a group of general formula $C_{1-6}$alkyl-O—.

The term "thio" or "thiol" as used herein refers to the —SH group. The term "isocyano" as used herein refers to the group of formula —N=C=O. The term "isothiocyano" as used herein refers to a group of formula —N=C=S.

In an embodiment, said organic molecule of Formula (III), (IV), (V), (VI), (VII), (VIII), (IX), (X), (XI) or (XII) can be optionally coupled to said at least one class C beta-lactamase using a multifunctional arm-spacer of Formula (XIII), (XIV), (XV), or (XVI),

   (XIII)

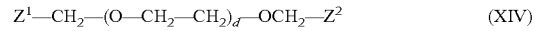   (XIV)

   (XV)

   (XVI)

wherein v is an integer selected from 2 to 12, for example, v is 2, 3, 4, 5, 6, 7, 8, 9, 10, 11, or 12;

d is an integer selected from 0 to 5, for example, d is 0, 1, 2, 3, 4, or 5;

t is an integer selected from 1 to 10, for example, t is 1, 2, 3, 4, 5, 6, 7, 8, 9, or 10;

$Z^1$, $Z^2$ are each independently selected from $N_3$-aryl, or $N_3$-aryl-$CH_2$—NH—CO—, optionally substituted with halogen, $C_{1-6}$alkyl or $C_{1-6}$alkoxy; diazirinyl; —COOH and N-hydroxysuccinimidyl ester thereof; —$CH_2$—$NH_2$ and N-maleimide or N-succinimide derivative thereof; —$CH_2OH$ and tosylates thereof; —$CH_2$—SH and dithiane derivatives thereof; —$CH_2N$=C=O; —$CH_2N$=C=S;

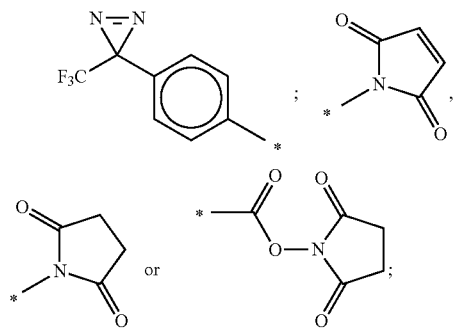

$W^1$ is selected from $N_3$-aryl, optionally substituted with halogen, $C_{1-6}$alkyl or $C_{1-6}$alkoxy; diazirinyl;

$W^2$ is selected from —COOH and N-hydroxysuccinimidyl ester thereof; —$CH_2$—$NH_2$ and N-maleimide or N-succinimide derivative thereof; —$CH_2OH$ and tosylates thereof; —$CH_2$—SH and dithiane derivatives thereof; —$CH_2N$=C=O; —$CH_2N$=C=S;

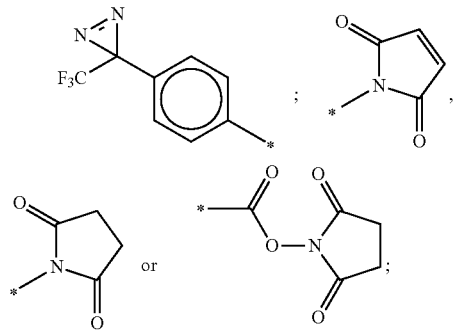

and $L^4$ and $L^5$ are defined as described above.

In an embodiment, the organic molecule of Formula (III), (IV), (V), (VI), (VII), (VIII), (IX), (X), (XI) or (XII) can be covalently coupled with a multifunctional arm-spacer of Formula (XIII), (XIV), (XV), or (XVI).

In an embodiment, for the binding of the class C beta-lactamase to the organic molecule of Formula (III), (IV), (V), (VI), (VII), (VIII), (IX), (X), (XI) or (XII) or to the multifunctional arm-spacer of Formula (XIII), (XIV), (XV), or (XVI) on the surface of the ATR element or the quartz crystal, N-maleimide or N-succinimide derivatives are preferred. For example, the N-maleimide derivative can be selected from

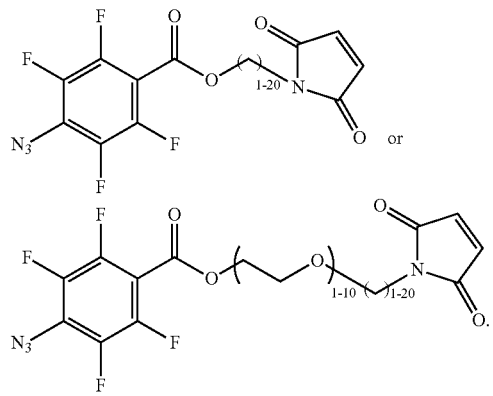

For example, the N-maleimide derivative can be

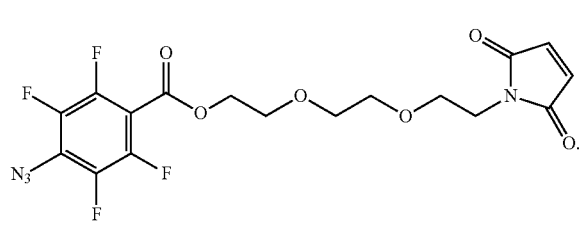 [SMILES: [N-]=[N+]=Nc1c(F)c(F)c(C(=O)OCCOCCOCCN2C(=O)C=CC2=O)c(F)c1F]

In an embodiment, the organic molecule of Formula (III), (IV), (V), (VI), (VII), (VIII), (IX), (X), (XI) or (XII) or the multifunctional arm-spacer of Formula (XIII), (XIV), (XV), or (XVI) is able to covalently couple the class C beta-lactamase by reacting with a functional group of said class C beta-lactamase.

The functional group of the class C beta-lactamase can be any group which allows coupling of said class C beta-lactamase with the organic molecule of Formula (III), (IV), (V), (VI), (VII), (VIII), (IX), (X), (XI) or (XII), or with the multifunctional arm-spacer of Formula (XIII), (XIV), (XV), or (XVI). The functional group can be a thiol group, a carboxyl group, an amine group, a hydroxyl group of a carbonyl group. Preferably, the functional group is a thiol group of the enzyme which can react with the organic molecule of Formula (III), (IV), (V), (VI), (VII), (VIII), (IX), (X), (XI) or (XII), or with the multifunctional arm-spacer of Formula (XIII), (XIV), (XV), or (XVI), such as maleimidyl, isothiocyanate or succinimidyl of said organic molecule of Formula (III), (IV), (V), (VI), (VII), (VIII), (IX), (X), (XI) or (XII), or of said multifunctional arm-spacer of Formula (XIII), (XIV), (XV), or (XVI). In a particular embodiment, the functional group is a thiol group present in a variant of a class C beta-lactamase comprising a cysteine in replacement of a native amino acid. More preferably, the functional group is a thiol group present in a variant of the wild type class C beta-lactamase of *Enterobacter cloacae* P99 which has been modified so as to have the alanine 266 replaced by a cysteine.

Using a class C beta-lactamase comprising a cysteine such as P99A266C is advantageous for coupling the class C beta-lactamase with the organic molecule of Formula (III), (IV), (V), (VI), (VII), (VIII), (IX), (X), (XI) or (XII) or with the multifunctional arm-spacer of Formula (XIII), (XIV), (XV), or (XVI), because the thiol group present in said cysteine at position 266 is available in the opposite direction of the active site and thus the coupling does not disturb the enzymatic activity of the class C beta-lactamase.

In an embodiment, the construction of a device comprising a class C beta-lactamase grafted on its surface comprises the steps of:

(a1)) chemically activating at least part of an ATR element's surface by oxidation, hydroxylation or reduction in acid or alkaline environment, or metal plating at least part of an ATR element's surface, or (a2) chemically activating at least part of a gold-plated quartz crystal surface by oxidation, hydroxylation or reduction in acid or alkaline environment, and (b) covalently grafting on said chemically activated or metal plated surface of step (a1) or (a2) an organic molecule of Formula (III), (IV), (V), (VI), (VII), (VIII), (IX), (X), (XI) or (XII). In an embodiment, said organic molecule of Formula (III), (IV), (V), (VI), (VII), (VIII), (IX), (X), (XI) or (XII) can be optionally further covalently coupled with a multifunctional arm-spacer of Formula (XIII), (XIV), (XV), or (XVI), prior to being reacted with a class C beta-lactamase.

The present invention provides a method for the measurement and/or quantification of a free beta-lactam antibiotic. The present method is adapted for monitoring beta-lactam antibiotic unbound to other biological molecules in biological samples. The invention is therefore advantageous in that it allows the measurement and/or quantification of the biologically active fraction of said beta-lactam antibiotics in a biological sample.

In an embodiment, the method of the present invention allows the label-free measurement of unbound beta-lactam antibiotic in a biological sample.

The invention is particularly useful to monitor the beta-lactam antibiotic dosage in a subject receiving a beta-lactam antibiotic therapy, e.g. antibiotherapy.

The biological samples of serum, blood, urine, interstitial fluid, saliva, tears, exudates, fluid collected from deep tissues, fluid collected from subcutaneous tissues or other mammal fluids, preferably human fluids, preferably serum, blood, urine, interstitial fluids, more preferably serum susceptible of containing a beta-lactam antibiotic, can be analyzed at regular intervals for a beta-lactam antibiotic.

In an embodiment of the present invention, the method comprises prior to step (c), the step of treating said sample with an aqueous solution. According to this embodiment, the sample is treated with an aqueous solution, prior to contacting at least one class C beta-lactamase with at least one biological sample.

The aqueous solution for the treatment of said biological sample can be selected from a buffer such as a phosphate buffer, or an aqueous solution comprising at least one salt and/or at least one organic compound such as a carbohydrate, a protein, a peptide, an amino acid, an organic acid (such as lactate), a polyol (such as mannitol or glycerol), a colloid (such as hydroxyethyl starch) or an infusion molecule, or any other compound capable of creating an osmotic pressure similar to that of the biological sample such as serum, at concentrations that preserve the chemical and physical intactness of the beta-lactam antibiotic to be measured.

By "phosphate" it is meant compounds from the group $M^1H_2PO_4$, $M^1_2HPO_4$, $M^1_3PO_4$, $M^2(H_2PO_4)_2$, $M^2_3(PO_4)_2$ and $M^2HPO_4$, wherein $M^1$ is Na, $L^1$, or K, and $M^2$ is Ca or Mg. Representatives of this group are $NaH_2PO_4$, $KH_2PO_4$, $Na_2HPO_4$, $K_2HPO_4$, $Mg(H_2PO_4)_2$.

By "salt" it is meant compounds of formula $M^3X^2$ or $M^4X^2_2$, wherein $X^2$ is selected from F, Cl, Br, I and $M^3$ is selected from Li, Na, K, $NH_4$ and alkylammoniums; $M^4$ is selected from Ca, Mg, Zn, Cu, Fe, Ni, Co.

The term "carbohydrate" as used herein includes monosaccharides, oligosaccharides and polysaccharides as well as substances derived from monosaccharides by reduction of the carbonyl group such as alditols, by oxidation of one or more terminal groups to carboxylic acids, or by replacement of one or more hydroxy group(s) by a hydrogen atom, an amino group, a thiol group or similar heteroatomic groups. It also includes derivatives of these compounds.

In an embodiment, the aqueous solution is preferably phosphate buffered saline (PBS).

The treatment of the biological sample with an aqueous solution prior to step (c) of the present method is preferably a dialysis step. Dialysis, preferably micro-dialysis allows to isolate the unbound fraction of a beta-lactam antibiotic for measurement. This is advantageous over the available commercial methods that do not separate free from bound fraction without an additional step such as centrifugation through membranes.

Advantageously, the method of the present invention allows that the biologically active beta-lactam antibiotics can be determined directly and without any additional step.

In an embodiment, the method is performed in vitro, or ex-vivo. In another embodiment, the method is performed in vivo.

In a further embodiment, the above described method is for the measuring and/or monitoring of a beta-lactam antibiotic in microdialysate. Microdialysis probes can be used to this effect. Preferably the microdialysate is derived from a subject receiving a beta-lactam antibiotic therapy, e.g. antibiotherapy, by in vivo microdialysis. This has the advantage that the number of sample preparation steps can be reduced. The measurement and/or monitoring of beta-lactam antibiotic levels in the biological sample can be obtained in a short time interval. Preferably, the invention provides a method as described above for the measuring and/or monitoring of a beta-lactam antibiotic in microdialysate from a subject receiving a beta-lactam antibiotic therapy, e.g. antibiotherapy, for example by in vivo microdialysis.

In an embodiment, the method for measuring and/or monitoring a free beta-lactam antibiotic in a biological sample such as in microdialysate from a subject receiving a beta-lactam antibiotic therapy may be performed at two or more successive time points and the respective outcomes at said successive time points may be compared, whereby the presence or absence of a change between the measurement of free beta-lactam antibiotic in the subject at said successive time points is determined. The method thus allows to monitor a change in the quantity or concentration of free beta-lactam antibiotic in biological samples of a subject over time.

In an embodiment, the microdialysis uses a probe which is inserted into tissue in vivo, such that one side of a semi-permeable membrane is in contact with tissue and extra cellular liquid and the other side is flushed or rinsed with a dialysis liquid (perfusate) which takes up substances from the extra cellular liquid through the membrane. A substance can also be distributed locally to the extra-cellular liquid through the perfusion liquid. These substances can then be analyzed in the dialysate on or after exiting the probe. Probes are often made in the form of an inner and an outer tube, where the outer tube exhibits a membrane and the dialysate and the perfusate is entering and exiting the tube at one end and the other end of the tubes are fused or plugged.

Microdialysis has the advantage of allowing the examination of the amounts present or missing of substances in patients. It also allows monitoring changes in the status of substances connected with the use of medicaments.

In a preferred embodiment, the present method is used for the monitoring of a subject being treated with at least one beta-lactam antibiotic, e.g. undergoing antibiotherapy. In an embodiment, the method increases treatment accuracy and reliability. As used herein the term "subject" or "patient" or "individual" refers to any vertebrate species. Preferably, the term subject encompasses warm-blooded vertebrates, more preferably mammals.

More particularly contemplated are mammals such as humans, as well as animals such as carnivores other than humans (such as cats and dogs), swine (pigs, hogs, and wild boars), poultry, ruminants (such as cattle, oxen, sheep, giraffes, deer, goats, bison, and camels), and horses.

In a further embodiment, the invention provides a method as described above for the measuring and/or monitoring a beta-lactam antibiotic in the treatment of an infection caused by Gram positive or Gram negative micro-organisms in a subject in need thereof.

Indeed, the present method ensures a rapid quantitative analysis of free beta-lactam antibiotics. The method is useful for monitoring and adjusting the amount of free antibiotics in a biological sample, such as in a subject's blood. The present method is particularly valuable in case of clinical treatment, for example, in case of treatment via continuous antibiotic infusion.

The present invention can be further illustrated by the following examples, although it will be understood that these examples are included merely for purposes of illustration and are not intended to limit the scope of the invention unless otherwise specifically indicated.

EXAMPLES

Example 1

Quantitative Measurement of Beta-lactam Antibiotics Using a Colorimetric Assay According to an Embodiment The colorimetric assay used the competition between a reporter substrate and a beta-lactam antibiotic towards the catalytic site of the class C beta-lactamase. In the absence of beta-lactam antibiotic, the class C beta-lactamase P99 hydrolyzed rapidly the reporter substrate and this reaction produced a deep red (nitrocefin) or yellow (CENTA) coloration.

In the presence of beta-lactam antibiotic, P99 catalytic activity was less available and thus less able to hydrolyze the reporter substrate. Accordingly, the higher the concentration of beta-lactam antibiotic, the lower the coloration of the medium. In this enzymatic competitive kinetic assay, the UV-Visible absorbance was inversely proportional to the concentration of beta-lactam antibiotic.

Scheme 1 shows the kinetic equations of the reaction of the wild type or variants class C beta-lactamase of *Enterobacter cloacae* P99 with a reporter substrate (S) and a beta-lactam antibiotic (I).

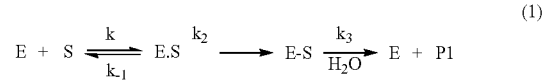

(1)

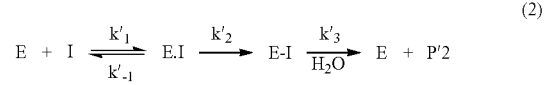

(2)

wherein
E=Enzyme (class C beta-lactamase),
S=Substrate (reporter substrate),
I=Inhibitor substrate (beta-lactam antibiotic),
E.S and E.I=Michaelis complexes (non covalent interactions),
E-S and E-I=Acyl-enzyme complexes (covalent interactions),
P1 and P'2=Products of reaction (hydrolyzed beta-lactam),
$k_2$ and $k'_2$=Acylation steps $K=k_1/k_{-1}$,
$k_3$ and $k'_3$=Deacylation steps $K'=k'_1/k'_{-1}$.

The difference relies upon the respective acylation ($k_2/K$ and $k'_2/K'$) and deacylation rates ($k_3$ and $k'_3$) or hydrolysis of the acyl-enzyme covalent complex:

$$k_3 > k_2/K \qquad (3)$$

$$k'_2/K' > k'_3 \qquad (4)$$

The reporter substrate (equations (1) and (3)) was rapidly hydrolyzed, while the beta-lactam antibiotic was slowly hydrolyzed (equations (2) and (4)). Advantageously, the hydrolysis rate of the beta-lactam antibiotic/class C beta-lactamase covalent complex was slow enough to allow the detection of this complex by spectroscopic methods.

Calibration with Standards

The different solutions used were prepared as follows.

Report substrate: A stock solution of reporter substrate consisting of 10 mM of CENTA in HEPES (4-(2-hydroxyethyl)-1-piperazineethanesulfonic acid) pH 7.8 (20 mM)/NaCl (200 mM) buffer was diluted 10 times in HEPES pH 7.8 (20 mM)/NaCl (200 mM) buffer.

Solution of enzyme: in a spectrophotometer cell, containing HEPES/NaCl buffer (400 μL) and CENTA (100 μL, 100 μM); 20 μL of P99 enzyme solution was added. The concentration of P99 enzyme was variable in function of the preparation and ranged between 0.01 mg/ml to 100 mg/ml. The absorbance variation was measured at 405 nm during 1 min. The enzyme solution used in the experiment was then diluted until the absorbance variation was comprised between 35 and 45 mUAbs/min cm$^{-1}$. This diluted solution was further used in this example.

A stock solution of piperacillin/tazobactam (TAZOCIN®, Pfizer, Belgium) was prepared by dissolving 5.9 mg of TAZOCIN® (corresponding to 5 mg of piperacillin) in 1 ml water. The resulting stock solution was diluted a 100 times by two serial 10 times dilutions in water to obtain a mother solution of 50 μg/ml piperacillin.

A stock solution of piperacillin was prepared by dissolving 5 mg of piperacillin (Sigma-Aldrich) in 1 ml of water. The resulting stock solution was diluted 100 times by two serial 10 times dilutions in water to obtain a mother solution of 50 μg/ml piperacillin.

A solution of temocillin (NEGABAN®, Eumedica Pharmaceuticals, Belgium) was prepared by dissolving 5.5 mg of NEGABAN® (corresponding to 4 mg of temocillin) in 1 ml of water. The resulting stock solution was diluted 100 times by two serial 10 times dilutions in water to obtain a mother solution of 40 μg/ml temocillin.

A solution of Pentrexyl® (Bristol-Myers Squibb, Belgium) was prepared by dissolving 5 mg of Pentrexyl® (corresponding to 5 mg of ampicillin sodium) in 1 ml of water. The resulting stock solution was 100 times diluted by two serial 10 times dilutions in water to obtain a mother solution of 50 μg/ml ampicillin.

The following standard solutions of beta-lactam antibiotics were prepared: TAZOCIN® and piperacillin: 50, 42.5, 35, 27.5, 20, 12.5, 5 and 0 µg/ml; NEGABAN®: 40, 34, 28, 22, 16, 10, 4 and 0 µg/ml; Pentrexyl®: 50, 42.5, 35, 27.5, 20, 12.5, 5 and 0 µg/ml.

Dilutions were made in water in the wells of a microplate with 96 wells, in a final volume of 40 µl for the 8 solutions of each beta-lactam antibiotic. To each well, 10 µl of 1 mM CENTA was added. The content of the wells for one set of standard is shown in Table 1.

TABLE 1

| Well number | Mother solution of beta-lactam antibiotic | water | 1 mM CENTA |
|---|---|---|---|
| A1 | 40 µl | 0 µl | 10 µl |
| A2 | 34 µl | 6 µl | 10 µl |
| A3 | 28 µl | 12 µl | 10 µl |
| A4 | 22 µl | 18 µl | 10 µl |
| A5 | 16 µl | 24 µl | 10 µl |
| A6 | 10 µl | 30 µl | 10 µl |
| A7 | 4 µl | 36 µl | 10 µl |
| A8 | 0 µl | 40 µl | 10 µl |

Measurements and Data Analysis 8 standard solutions per antibiotic tested were deposited on a 96-well microplate (40 µL). 10 µL of CENTA (1 mM) was added in each well as shown in Table 1.

The absorbance was measured using a microplate reader, with each column being measured separately. The program comprised following the kinetic during 4 min, with 1 measure at 405 nm every 10 seconds (24 measures). In each well and simultaneously, a mixture of 45 µl HEPES/NaCl buffer and 5 µl P99 solution was added. The same mixture was used for the 8 wells of each column, and thus prepared in advance for distribution with a multi-channel pipette. After 1 min incubation at 20° C., the reading was started, and KC Junior™ software (BioTek Instruments, Winooski, Vt.) was used to calculate the slope of each reaction kinetic. The experiments were made in triplicate and reproduced over 5 different days.

The slope obtained for well number 8 corresponded to the maximum of enzyme activity (concentration of beta-lactam antibiotic=0 µg/ml) and was considered as 100%. The slopes corresponding to wells 1 to 7 were expressed as percentages of residual activity.

Figure 2:
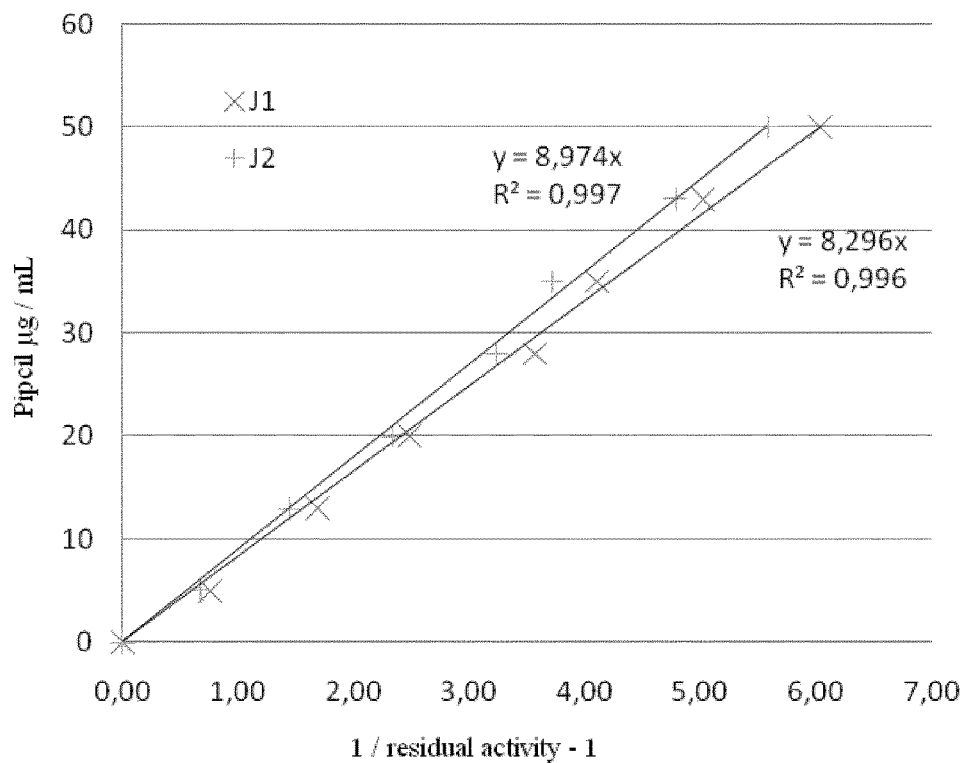
FIG. 2 represents a graph plotting the concentration of antibiotic as a function of the inverse of residual rate expressed as % of residual activity during two different days J1 and J2.

The results of the measurements are shown in FIGS. 1A to 1D, wherein are plotted the percentage of enzyme activity as a function of the concentrations of beta-lactam antibiotic. Linearization was obtained by plotting the concentration of beta-lactam antibiotic in function of the inverse of residual rate expressed as percentage of residual activity. The plot is shown in FIG. 2.

Determination of Beta-lactam Antibiotic Concentration in Biological Samples

Test samples were collected on patient using Microdialysis probes (CMA/20 Elite probe, 14/10 PAES, CMA Microdialysis AB, Stockholm, Sweden). The syringe used where BAS MDN-0100 1 mL syringe from BASi, West Lafayette, USA. Probes were attached to microdialysis pumps (CMA 400 syringe pump from CMA Microdialysis AB, Sweden). Human serum was obtained (i) from a commercial source (Lonza); (ii) from volunteers for normal serum; or (iii) from hospitalized patients. The antibiotic mother solutions were prepared as described above. The following standard solutions were used: TAZOCIN® and piperacilin: 50, 25, 12.5, 6.25 and 0 µg/ml; NEGABAN®: 40, 20, 10, 5 and 0 µg/ml.

The standard solutions (40 µl final volume) were placed on the 96-well microplate, column by column in wells number 1 to 5.

The biological samples were placed in wells number 6 to 8 (triplicate, final volume 40 µl). The content of each well is listed in Table 2. 10 µl of 1 mM of CENTA was added in each well (Table 2).

TABLE 2

| Well number | water | 1 mM CENTA |
|---|---|---|
| Standard solution of beta-lactam antibiotic | | |
| A1 | 40 µl | 0 µl | 10 µl |
| A2 | 20 µl | 20 µl | 10 µl |
| A3 | 10 µl | 30 µl | 10 µl |
| A4 | 5 µl | 35 µl | 10 µl |
| A5 | 0 µl | 40 µl | 10 µl |
| Biological sample | | |
| A6 | 40 µl | 0 µl | 10 µl |
| A7 | 40 µl | 0 µl | 10 µl |
| A8 | 40 µl | 0 µl | 10 µl |

The reaction kinetic were followed using a microplate reader, column by column as described herein above (calibration section), after the simultaneous addition of P99 in the 8 wells of one column (50 µL of HEPES/NaCl (45 µL) and enzyme solution (5 µL)).

The slope recorded for well number 5 corresponded to 100% of enzyme activity. The slopes recorded for wells number 1 to 4 were used to obtain the calibration curve. The concentration of the beta-lactam antibiotic in the biological samples (in triplicate, wells numbers 6 to 8) was evaluated by comparison with the calibration curve (accuracy 5%).

Example 2

Preparation a Variant of *Enterobacter cloacae* P99 Beta-lactamase with the Alanine 266 Replaced by a Cysteine

*E. coli* strains DH5α and BL21(DE3) were used as hosts for the construction of expression plasmids and for protein expression, respectively. The plasmids, PCR-Script Amp (Agilent Technologies) and pET28-a(+) (Clontech) were used as cloning and expression vectors respectively. Cells were grown in Luria-Bertani (LB) medium supplemented with 25 µg kanamycin/ml at 37° C.

For the construction of expression plasmids, the P99 gene from genomic DNA from *Enterobacter cloacae* P99 initially isolated, was PCR-amplified with primers P99_ncol (forward primer, SEQ ID No. 1) and P99_xhoi (reverse primer, SEQ ID No. 2) (listed in Table 3).

TABLE 3

| Name | SEQ ID No. | Nucleic acid sequence |
|---|---|---|
| P99_ncoi | 1 | AACCATGGCGCCAGTGTCAGAAAAACA |
| P99_xhoi | 2 | AACTCGAGCGCCTCAAGGATATGGTATGCCG |

PCR was carried out using pfu DNA polymerase (Promega) and the PCR product cloned into PCR-Script Amp (Agilent Technologies) and sequenced. The P99 sequence was subcloned into the NcoI and XhoI sites of the pET28-a (+) vector to give the pET28-P99 expression plasmid.

Site-directed Mutagenesis

Site-directed mutagenesis was performed using the Quickchange Site-Directed Mutagenesis Kit (Agilent Technologies) according to the manufacturer's instructions. pET28-P99 was used as a template, and the synthetic oligonucleotide primers were P99_A266C+(SEQ ID No. 3) and P99_A266C– (SEQ ID No. 4) (listed in Table 4). Putative positive clones were picked, and plasmids were isolated and sequenced. The nucleic acid sequences of P99 (SEQ ID NO.5) and P99A266C (SEQ ID NO.7) are respectively shown in FIGS. 5 and 7.

TABLE 4

| Name | SEQ ID No. | Nucleic acid sequence |
|---|---|---|
| P99_A266C+ | 3 | CCGGAGAACGTTGCTGATTGCTCACTTAAGC AGGGC |
| P99_A266C– | 4 | GCCCTGCTTAAGTGAGCAATCAGCAACGTTC TCCGG |

Protein Expression

For protein expression, transformed pET28-P99 *E. coli* BL21 colonies were grown in LB medium containing 25 µg kanamycin/ml to an OD600 of 0.8, induced for 3 h with 0.5 mM IPTG, and finally harvested by centrifugation and resuspended in 20 mM HEPES, 200 mM NaCl pH8 buffer. Intracellular recombinant proteins were released with NS 100 µL Panda Homogenizer and Cell debris were removed by centrifugation.

Protein Purification

The supernatant was loaded onto a 5 ml HisTrap™ column (GE Healthcare) loaded with $Ni^{2+}$ ions and equilibrated in binding buffer (20 mM HEPES, 200 mM NaCl, and 10 mM imidazole [pH 8]). The column was washed until the absorbance returned to baseline.

Elution of P99 protein was performed by the use of a step gradient. The column was washed with a solution containing 100 mM imidazole. The protein was then eluted in binding buffer containing 250 mM imidazole and dialyzed in 20 mM HEPES, 200 mM NaCl pH 8 buffer.

The protein expression and purification of P99A266C was performed according to the same procedure. The amino acid sequences of P99 (SEQ ID NO.6) and P99A266C (SEQ ID NO.8) are respectively shown in FIGS. 6 and 8.

Enzyme Activity

Kinetic assays with the P99 beta-lactamase and with P99A266C beta-lactamase were performed in order to test and compare the enzyme activities. The results are shown in Table 5. As illustrated in Table 5, the mutation of alanine at position 266 to cysteine in P99 beta-lactamase did not affect the enzyme activity.

Example 3

Construction of a Biosensor for Beta-lactam Antibiotics According to an Embodiment of the Present Invention Triangular-shaped germanium crystal ($4.8\times4.8\times45$ mm$^3$) purchased from Biosentech (Belgium) was degreased successively with acetone (15 ml) and methanol (15 ml) under ultrasounds (40 KHz, 22° C., 100% power) during 10 min for each solvent. The crystal was surface-oxidized as follows: The germanium crystal was washed with 38% $HNO_3$ (1 min) and rinsed with milliQ water. Oxidation was performed with 99+% oxalic acid/35% $H_2O_2$ (10:90, v/v) during 5 min at 20° C., and washing with milliQ water. This was repeated three times. The device was dried under $N_2$ flux (10 min).

The surface oxidized crystal was then reacted with the organosilane molecule $(C_2H_5O)_3Si—CH_2—CH_2—CH_2—NH—COO—(CH_2—CH_2—O)_6—CH_2—CH_2—OCH_3$. The silane (2,5,8,11,14,17,20-heptaoxadocosan-22-yl-3(triethoxysilyl)-propylcarbamate) was prepared according to Devouge et al. (2009, J. Colloid Interface Sci., 332, 408-415).

The surface oxidized crystal was immersed into 2% silane solution in $CCl_4$, under $N_2$ atmosphere, during 2 h at reflux. The crystal was washed with methanol (2 h) and with dichloromethane (2 h) in a Soxhlet apparatus.

Next, the surface of the silanated crystal was photografted with a tetrafluorophenyl azido-maleimide of the following formula $N_3—C_6F_4—COO—(CH_2—CH_2—O)_2—CH_2—CH_2—N—(CO—CH—)_2$. This azide was prepared as follows: To 1-(2-{2-[2-(2-Hydroxy-ethoxy)-ethoxy]-ethyl)-pyrrole-2,5-dione (prepared as described in U.S. Pat. No. 5,144,043) (1 equiv., 0.3 mmol), 1-ethyl-3-(3-dimethylaminopropyl)carbodiimide (EDCI) (1.3 equiv.), 4-azido-2,3,5,6-tetrafluorobenzoïc acid (1 equiv.) (prepared according to Keana and Cai, 1990, J. Org. Chem. 55, 3640) under argon atmosphere was added DMAP (catalytic amount) in dry dichloromethane (2 ml). The mixture was stirred for 4 h at 0° C. and then filtered. The filtrate was evaporated and the residue was dissolved in EtOAc (5 ml), washed twice with brine then with distilled water. The combined organic layers were dried over $MgSO_4$, filtered and concentrated under vacuum to afford the desired product as brown oil (46% yield).

For photografting the tetrafluorophenyl azido-maleimide, a solution of tetrafluorophenyl azido-maleimide in benzene (5 mg/1.5 ml) was sprayed on the device and the solvent was evaporated under air flux in the dark to obtain a deposition of 0.1 to 0.2 mg/cm$^2$. The crystal was submitted to UV irradiation during 2 h at room temperature (3 lamps of 8 W and lambda$_{max}$ 254 nm, placed at a distance of 10 cm). The device was rinsed with THF (10 min) and $CHCl_3$ (5 min)

TABLE 5

| | TAZOCIN | | | Piperacillin | | | NEGABAN | | |
|---|---|---|---|---|---|---|---|---|---|
| ug/ml | P99 mUAbs/min | P99A266C mUAbs/min | Diff. (%) | P99 mUAbs/min | P99A266C mUAbs/min | Diff. (%) | P99 mUAbs/min | P99A266C mUAbs/min | Diff. (%) |
| 40 | 2.2 | 2.3 | –5% | 2.4 | 2.5 | –4% | 5.3 | 5.4 | –2% |
| 20 | 4.0 | 3.8 | 7% | 4.0 | 3.8 | 6% | 7.5 | 7.5 | –1% |
| 10 | 5.9 | 6.2 | –4% | 6.4 | 6.1 | 4% | 9.4 | 9.6 | –2% |
| 5 | 8.0 | 8.5 | –6% | 9.7 | 8.3 | 16% | 11.3 | 11.5 | –2% |
| 0 | 17.4 | 17.1 | 2% | 16.4 | 16.0 | 2% | 15.6 | 15.2 | 2% | under shaking at 20° C. (Unimax 1010 Heidolph, 150 rpm), and provided the activated surface. The above described procedure resulted in an N-maleimide-functionalized ATR element, as schematically illustrated here below.

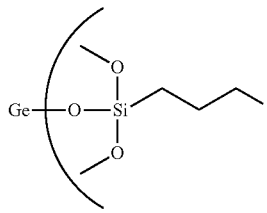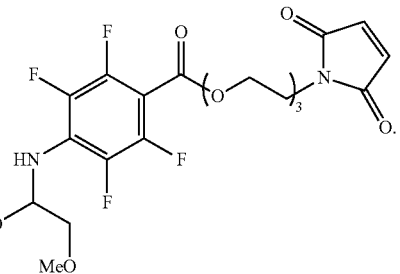

On the N-maleimide functionalized ATR element, the class C beta-lactamase P99A266C prepared as in example 2 was bound.

P99A266C binding onto the functionalized crystal was obtained by depositing 10 µL of a solution (phosphate buffer 50 mM, pH 7) of P99A266C enzyme (30 µg/ml) during 1 h, then rinsing with buffer during 15 min at a rate of 35 µL/min.

Figure 3:
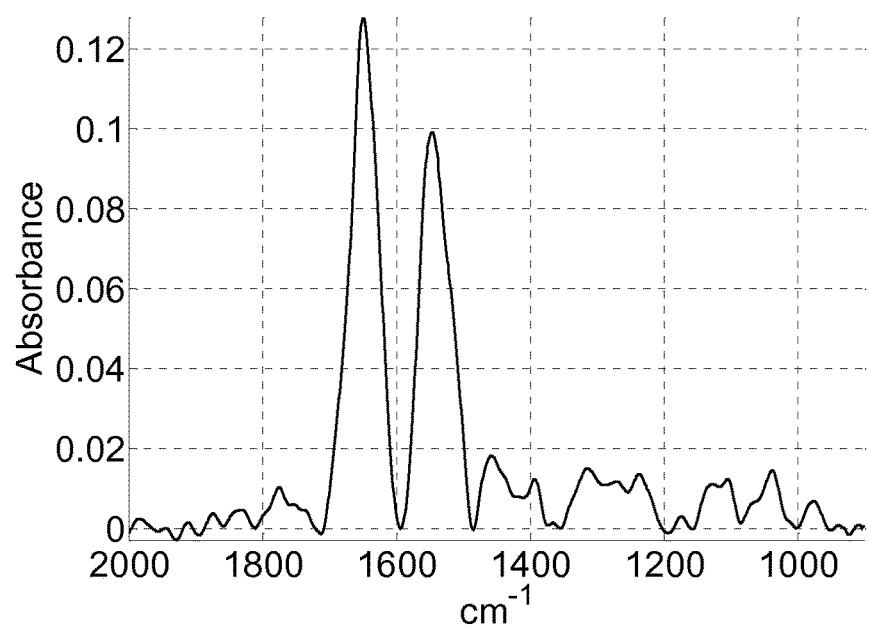
FIG. 3 represents a graph representing the IR spectrum of the class C beta-lactamase P99A266C grafted on N-maleimide-functionalized germanium ATR element.

The binding of P99A266C to the functionalized ATR element was monitored by FTIR-ATR spectroscopy (Goldzstein et al., 2009, Biosensors and Bioelectronics, 24, 1831-1836). Attenuated Total Reflection Fourier Transformed Infrared (ATR-FTIR) spectra were obtained on a Brüker IFS55 FTIR spectrophotometer (Ettlingen, Germany) equipped with a MCT detector (broad band 12000-420 $cm^{-1}$, liquid $N_2$ cooled, 24 h hold time) at a resolution of 2 $cm^{-1}$ with an aperture of 3.5 mm and acquired in the double-sided, forward-backward mode. Two levels of zero filling of the interferogram prior to Fourier transform allowed encoding the data every 1 $cm^{-1}$. The spectrometer was continuously purged with dry air (Whatman 75-62, Haverhill, Mass., USA). The P99A266C functionalized crystal was accommodated on the beam condenser from a Golden Gate Micro-ATR from Specac. A top plate with a groove fitting the crystal was used in replacement of the diamond-bearing plate (WOW Company, Belgium). With this geometry, a single reflection was obtained and more than 10 lanes can be used on a crystal. As shown in FIG. 3, IR spectroscopy of the P99A266C grafted on the ATR showed the amide I and II stretching bands (~1650 $cm^{-1}$ and ~1550 $cm^{-1}$) of P99A266C (mean of 254 scans).

The grafting of P99A266C to the ATR was further controlled as follows: Two channels (channel 1 and channel 2) of a surface oxidized ATR device were both grafted with a silane as described above and subsequently photografted with the above described maleimide compound. Channel 2 of the device was subsequently passivated with mercaptoethanol (1 mM solution in water, 10 µl/min, 170 min). A solution of P99A266C was passed over both channels. The binding of P99A266C to the functionalized ATR element was monitored by FTIR-ATR spectroscopy. The results are shown in FIGS. 4B and 4C. FIG. 4B illustrates a graph representing the IR spectrum of the maleimide-functionalized germanium ATR channel contacted with P99A266C (a) in the absence of mercaptoethanol passivation and (b) after mercaptoethanol passivation of the channel.

FIG. 4C show the binding of P99A266C on the N-maleimide-functionalized germanium ATR channels as function of time (a) in the absence of mercaptoethanol passivation and (b) after mercaptoethanol passivation of the channel.

Figure 4A:
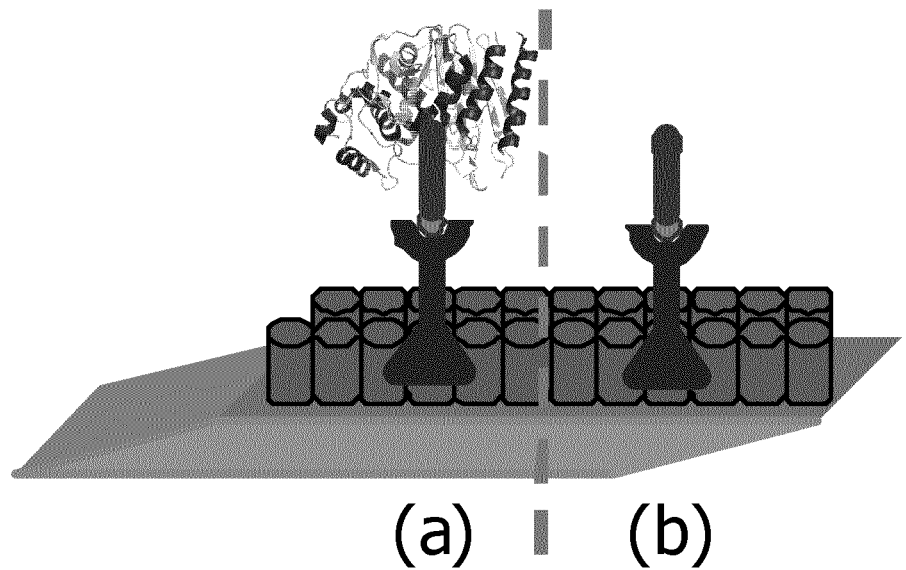
FIG. 4A represents a schematic representation of the fixation of P99A266C on the functionalized ATR device (a) without mercaptoethanol passivation and (b) with mercaptoethanol passivation.
Figure 4B:
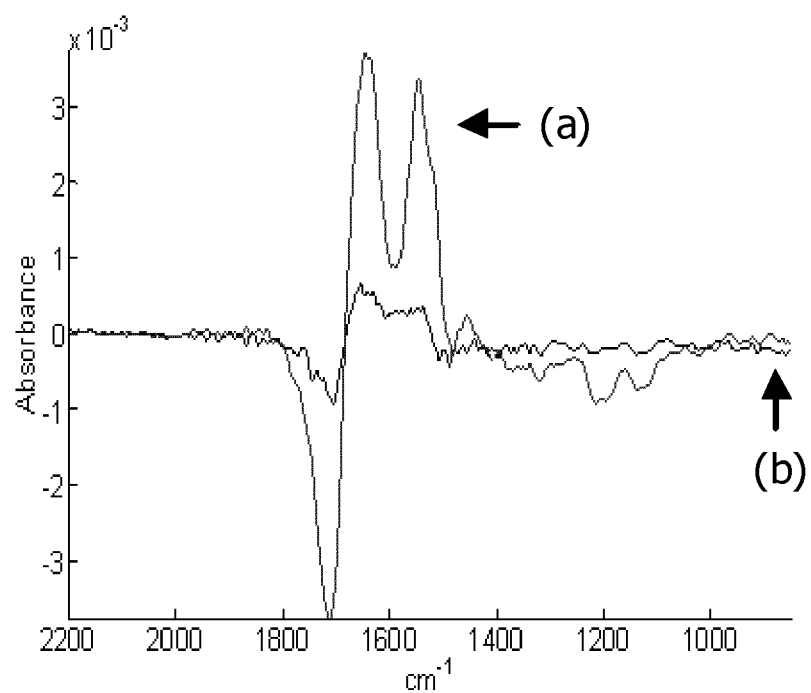
FIG. 4B represents a graph representing the IR spectra of N-maleimide-functionalized germanium ATR channel contacted with P99A266C (a) in the absence of mercaptoethanol passivation and (b) after mercaptoethanol passivation of the channel.

As shown in FIGS. 4B and 4C, when passing a solution of P99A266C over both channels, comparatively to channel 1 of the device, which was not passivated, channel 2 was unable to fix P99A266C. This is also schematically illustrated in FIG. 4A. The enzyme was thus well anchored via the thiol of the cysteine at position 266 reacting with the maleimide function of the device.

The immobilized enzyme was able to react rapidly with its chromogenic substrate CENTA: this was controlled by the appearance of the red coloration. When a beta-lactam antibiotic (for instance cefuroxim) present in a sample was fixed on the receptor, the reaction with its chromogenic substrate did not occur as expected because the active site was occupied.

Example 4

Quantitative Measurement of Beta-lactam Antibiotic Using a Biosensor

A solution of the beta-lactam antibiotic cefuroxim; obtained from Sigma-Aldrich in milliQ water at a concentration of 50-100 µg/mL was passed over the biosensor constructed in Example 3. The solution was passed over the crystal during 10-20 min at a rate of 35 µl/min.

FTIR-ATR spectra were recorded and cefuroxim binding was monitored by following the appearance of its characteristic signal. By subtracting the spectrum of the P99A266C, the spectrum of the acyl-enzyme complex appeared clearly. The intensity of the peak at 1730 $cm^{-1}$ allowed the quantitative measurement of cefuroxim binding. It was seen that the azetidinone function at 1800 $cm^{-1}$ had been transformed into an ester bond (~1730 $cm^{-1}$) when cefuroxim was fixed to P99A266C (acyl-enzyme complex) comparatively to the reference spectrum of cefuroxim. The structure of the acyl-enzyme complex is represented below.

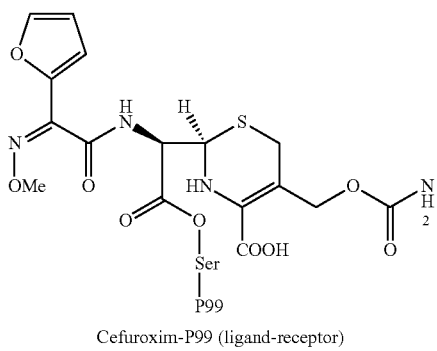

Cefuroxim-P99 (ligand-receptor)

Consequently, Example 4 shows that by using a device such as for example a biosensor, the present method allows the measurement of beta-lactam antibiotics in biological samples.

Example 5

Comparison Between a Class a Beta-lactamase (Tem-1 Penicillinase) and a Class C Beta-lactamase (*Enterobacter cloacae* P99) for the Determination of Ampicillin Concentrations in Solution In order to determine the concentration of ampicillin in a solution, two beta-lactamases were compared, in particular the class A beta-lactamase (penicillinase) TEM-1 (UniProt: C514X2_ECOLX) and the class C beta-lactamase of *Enterobacter cloacae* P99 described in Example 1.

The dilution buffer for the enzymes, nitrocefin (CPR), standards and samples was 50 mM PBS buffer, pH 7. The stock solution of CPR was 200 µM. The standard solution of ampicillin was prepared at concentrations of 100, 75, 50, 30, 15, 5, 1 and 0 mg/L.

In the method 2 (BLAC2), 99 µl of sample, 99 µl of CPR and 22 µl of enzyme, i.e. Tem-1 or P99, were mixed. The enzyme activity ($v_{0\ max}$) was adjusted at +/−0.2 $\Delta Abs_{482}$/min.

The effect of ampicillin concentration on the rates ($\Delta Abs_{482}$/min) of P99 or Tem-1 catalyzed reaction at fixed concentration of CPR are shown in FIG. 9. This example demonstrates that when using a class A enzyme, no inhibition of the reaction was observed in the presence ampicillin even at 100 mg/L (FIG. 9, Tem-1). It was therefore not possible to determine the presence or the concentration of ampicillin in solution using a class A beta-lactamase such as the penicillinase Tem-1.

Conversely, as already described in Example 1, the class C P99 beta-lactamase allowed the determination of ampicillin concentrations ranging from 0 to 100 mg/L.

Example 6

Determination of Standard Curves of a Large Variety of Beta-lactam Antibiotics Using a Method According to an Embodiment of the Present Invention The standard curves of the beta-lactam antibiotics listed in Table 6 were determined using a method according to an embodiment of the present invention. The standard curves of the beta-lactam antibiotics listed in Table 6 were determined using either the method 1 or 2.

The dilution buffer for P99, nitrocefin (CPR) and antibiotics was 50 mM PBS buffer, pH 7. The stock solution of CPR was 200 µM. The standard solution of antibiotics was prepared at concentrations of 100, 75, 50, 30, 15, 5, 1 and 0 mg/L.

In the method 1 (BLAC1), 10 µl of standard solution of antibiotics, 100 µl of CPR and 100 µl of P99 enzyme were mixed. The enzyme activity NO max) was adjusted at +/−0.2 $\Delta Abs_{482}$/min.

In the method 2 (BLAC2), 99 µl of standard solution of antibiotics, 99 µl of CPR and 22 µl of P99, were mixed. The enzyme activity ($v_{0\ max}$) was adjusted at +/−0.2 $\Delta Abs_{482}$/min.

Table 6 lists the beta-lactam antibiotics of which the standard curves were determined using a method according to an embodiment of the present invention.

TABLE 6

| Antibiotics | Class |
|---|---|
| benzylpenicillin | Penams |
| methicillin | |
| oxacillin | |
| cloxacillin | |
| piperacillin, | |
| temocillin | |
| amoxicillin | |
| ampicillin | |
| azlocillin | |
| cephalexin | Cephalosporins |
| cefdinir | |
| cefoperazone | |
| ceftizoxime | |
| cefuroxime | |
| cefoxitin | |
| Ceftaroline | |
| ceftriaxone | |
| cefotaxime | |
| cefpodoxime | |
| ceftazidime | |
| meropenem | Penems |
| ertapenem | |
| aztreonam | Monobactam |
| Tazobactam | Beta-lactamase inhibitor/penam sulfone |

Example 7

Determination of the Individual Concentrations of a Mixture of Two Beta-lactam Antibiotics The individual concentrations of two beta-lactam antibiotics in solution were determined using a class C beta-lactamase such as the class C beta-lactamase of *Enterobacter cloacae* P99 in combination with a second beta-lactamase different from P99.

Combination of Data Obtained with Class C P99 Beta-Lactamase and Data Obtained with a Class D Beta-lactamase Two different enzymes a class C beta-lactamase and a class D beta-lactamase were used to quantify the individual concentration of beta-lactam in a mixture containing ampicillin and cefuroxime.

From (eq.3) given above in the description:

$$Y_{p99}=a_1C_A+b_1+a_2C_C+b_2 \qquad \text{(eq. 4)}$$

wherein $C_A$ and $C_C$ are respectively the ampicillin and cefuroxime concentration (mg/L).

Rearranging (eq.4) to solve:

$$C_A = \frac{Y_{P99} - a_2 C_C - b_2 - b_1}{a_1} \quad \text{(eq. 4.1)}$$

Rearranging (eq.4) to solve:

$$C_C = \frac{Y_{P99} - a_1 C_A - b_1 - b_2}{a_2} \quad \text{(eq. 4.2)}$$

From (eq.3):

$$Y_{Oxa} = a_3 C_A + b_2 + a_4 C_C + b_4 \quad \text{(eq.5)}$$

Rearranging (eq.5) to solve $$C_A = \frac{Y_{Oxa} - a_4 C_C - b_4 - b_3}{a_3} \quad \text{(eq. 5.1)}$$

Rearranging (eq.5) to solve:

$$C_C = \frac{Y_{Oxa} - a_3 C_A - b_3 - b_4}{a_4} \quad \text{(eq. 5.2)}$$

From equations (eq.4.1) and (eq.5.1), $C_C$ can be determined:

$$C_C = \frac{a_1 Y_{Oxa} - a_3 Y_{P99} - a_1 b_4 - a_1 b_3 + a_3 b_2 + a_3 b_1}{a_1 a_4 - a_2 a_3} \quad \text{(eq. 6.1)}$$

From equations (eq.4.2) and (eq.5.2), $C_A$ can be determined:

$$C_A = \frac{a_2 Y_{Oxa} - a_4 Y_{P99} - a_2 b_3 - a_2 b_4 + a_4 b_1 + a_4 b_2}{a_2 a_3 - a_1 a_4}. \quad \text{(eq. 6.2)}$$

Class C beta-lactamase used was P99 beta-lactamase of *Enterobacter cloacae* P99 as described in Example 1.

Class D beta-lactamase was Oxa-29 enzyme (UniProt: Q9AEF8_9GAMM).

The dilution buffer for the enzymes, CPR, standards and samples was 50 mM PBS buffer, pH 7.0.

The stock solution of CPR was 200 μM. Standards solution of ampicillin and cefuroxime were prepared at 100, 75, 50, 30, 15, 5, 1 and 0 mg/L.

In the method 1 (BLAC1), 10 μl of 50-fold diluted sample, 100 μl of CPR and 100 μl of enzyme P99 were mixed. The reaction kinetics was determined by measuring the absorbance at 482 nm as a function of time. Enzyme activity $v_{0\,max}$ was adjusted at +/−0.33 $\Delta Abs_{482}$/min.

In the method 2 (BLAC2), 99 μl of sample, 99 μl of CPR and 22 μl of enzyme Oxa-29 were mixed. The reaction kinetics was determined by measuring the absorbance at 482 nm as a function of time. Enzyme activity $v_{0\,max}$ was adjusted at +/−0.2 $\Delta Abs_{482}$/min.

Table 7 gives the rate ($\Delta Abs_{482}$/min) of Oxa-29 class D beta-lactamase and P99 class C beta-lactamase as a function cefuroxime and ampicillin concentrations.

TABLE 7

| | Method | | | |
|---|---|---|---|---|
| | BLAC2 ($\Delta Abs_{482}$/min) | | BLAC1 ($\Delta Abs_{482}$/min) | |
| | Enzyme | | | |
| | Oxa-29 Class D beta-lactamase | | P99 class C beta-lactamase | |
| mg/L | Cefuroxime | Ampicillin | Cefuroxime | Ampicillin |
| 0 | 0.2228 | 0.1919 | 0.3403 | 0.3233 |
| 1 | 0.2079 | 0.1831 | 0.3247 | 0.3221 |
| 5 | 0.2025 | 0.1680 | 0.2763 | 0.3207 |
| 15 | 0.2011 | 0.1532 | 0.1938 | 0.3164 |
| 30 | 0.1992 | 0.1292 | 0.1417 | 0.3114 |
| 50 | 0.1897 | 0.1056 | 0.0957 | 0.3008 |
| 75 | 0.1796 | 0.0869 | 0.0736 | 0.2909 |
| 100 | 0.1749 | 0.0730 | 0.0539 | 0.2806 |

Table 8 illustrates the residual rate minus 1, $(v_{omax}/v_0)-1$ (see eq. 2), of Oxa-29 class D beta-lactamase and P99 class C beta-lactamase as a function of cefuroxime and ampicillin concentrations; a and b are the linear regression coefficient of the data (Y=aX+b).

TABLE 8

| | Method | | | |
|---|---|---|---|---|
| | BLAC2 | | BLAC1 | |
| | Enzyme | | | |
| | Oxa-29 Class D beta-lactamase | | P99 class C beta-lactamase | |
| mg/L | Cefuroxime | Ampicillin | Cefuroxime | Ampicillin |
| 0 | 0.000 | 0.000 | 0.000 | 0.000 |
| 1 | 0.072 | 0.048 | 0.048 | 0.004 |
| 5 | 0.100 | 0.142 | 0.232 | 0.008 |
| 15 | 0.108 | 0.253 | 0.756 | 0.022 |
| 30 | 0.118 | 0.485 | 1.402 | 0.038 |
| 50 | 0.174 | 0.817 | 2.556 | 0.075 |
| 75 | 0.241 | 1.208 | 3.624 | 0.111 |
| 100 | 0.274 | 1.629 | 5.314 | 0.152 |
| | 4 | 3 | 2 | 1 |
| a | 0.0023 | 0.0159 | 0.0518 | 0.0015 |
| b | 0.0003 | 0.0002 | 0.0013 | 0.0000 |

Sample 1 was a spiked sample containing 40 mg/L of ampicillin and 60 mg/L of cefuroxime. Sample 2 was a spiked sample containing 70 mg/L of ampicillin and 30 mg/L of cefuroxime. In the spiked samples, the beta-lactam antibiotics were added to the buffer. The samples allowed to prove that the method allows the determination of the concentration of the beta-lactam antibiotics in the sample.

In order to determine the individual concentrations of the two antibiotics in the samples 1 and 2, we measured the initial rate of the samples with the enzyme P99 and Oxa. Maximum rate was also measured with the two enzymes. The 8 rates and the regression parameters of the standard curves were applied to the formulas eq.6.1 and eq.6.2. The concentrations of cefuroxime and ampicillin in sample 1 and 2 were calculated; the results are given in Table 9 and 10 respectively.

TABLE 9

Calculated concentrations of cefuroxime and ampicillin in sample 1

Sample 1

| | |
|---|---|
| $v_{0\ P99}$ ($\Delta Abs_{482}$/min) | 0.0659 |
| $v_{max\ P99}$ ($\Delta Abs_{482}$/min) | 0.3063 |
| $v_{0\ Oxa}$ ($\Delta Abs_{482}$/min) | 0.1078 |
| $v_{max\ Oxa}$ ($\Delta Abs_{482}$/min) | 0.1930 |
| $Y_{P99}$ | 3.648 |
| $Y_{Oxa}$ | 0.790 |

| | Calculated | Expected |
|---|---|---|
| $C_A$ (mg/L) | 40 | 40 |
| $C_C$ (mg/L) | 69 | 60 |

TABLE 10

Calculated concentrations of cefuroxime and ampicillin in sample 2

Sample 2

| | |
|---|---|
| $v_{0\ P99}$ ($\Delta Abs_{482}$/min) | 0.125 |
| $v_{max\ P99}$ ($\Delta Abs_{482}$/min) | 0.307 |
| $v_{0\ Oxa}$ ($\Delta Abs_{482}$/min) | 0.0855 |
| $V_{max\ Oxa}$ ($A\Delta Abs_{482}$/min) | 0.1920 |
| $Y_{P99}$ | 1.456 |
| $Y_{Oxa}$ | 1.246 |

| | Calculated | Expected |
|---|---|---|
| $C_A$ (mg/L) | 74 | 70 |
| $C_C$ (mg/L) | 26 | 30 |

Combination of Data Obtained with Class C P99 Beta-lactamase and Data Obtained with a Class B Beta-lactamase Two different enzymes, P99 class C beta-lactamase and a class B beta-lactamase are also used to quantify the individual concentration of beta-lactam in a mixture containing cefotaxime and cefuroxime.

Example 8

Determination of the Concentration of Two Different Beta-lactam Antibiotic Using Class C Beta-lactamase and a Separation Method

This example shows that it is possible to determine the concentration of two different beta-lactam antibiotics using class C beta-lactamase, using a prior separation step.

The kinetic of inhibition of class C P99 beta-lactamase by two beta-lactam antibiotics is described by the following equation:

$$Y_{1+2}=a_1C_1+b_1+a_2C_2+b_2,$$

where $C_1$ and $C_2$ are the concentrations of beta-lactam antibiotics inhibitors 1 and 2 respectively.

If beta-lactam antibiotic 2 is eliminated, the equation is reduced to $$Y_1=a_1C_1+b_1$$

By combination of $Y_{1+2}$ and $Y_1$, the individual concentration of the two beta-lactam antibiotics can be deduced.

Separation step:

An Amprep Octadecyl C18 minicolumn was used for this step. The column was rinsed with 1 ml of methanol. The column was equilibrated with 2 ml of 20 mM citrate buffer pH 3.1 (buffer).

Three samples were loaded:

Sample 1: 500 µl of aztreonam (50 mg/L)

Sample 2: 500 µl of ampicillin-fluorescein (ampi-flu) at 50 mg/L

Sample 3: Mixture of 500 µl of sample 1 and 500 µl of sample 2

Samples were applied on the column, washed with 2 ml of buffer and 1 ml fractions were collected with buffer containing from 10 to 50% of acetonitrile. Absorbance at 254 nm was measured for each fraction. The results are shown in FIG. 10 as a graph plotting the absorbance at 254 nm of fractions collected from the column after the loading of the sample 1, or 2 or 3 and separation using buffer containing from 10 to 50% acetonitrile.

Assessing Beta-lactam Concentration

Class C beta-lactamase used was P99 beta-lactamase as described in Example 1. The dilution buffer for the enzyme, nitorcefin (CPR), standards and samples was 50 mM PBS buffer, pH 7.0. The stock solution of CPR was 200 µM. Standard solutions of ampi-flu and aztreonam were prepared at 10, 7.5, 5, 3, 1.5, 0.5, 0.1 and 0 mg/L.

In the BLAC1 method, 10 µl of sample diluted 15-fold (aztreonam) or 30-fold (mixture of ampi-flu and aztreonam) were mixed with 100 µl of CPR and 100 µl of P99 Enzyme. The enzyme activity NO max) was adjusted at +/−0.30 $\Delta Abs_{482}$/min.

Table 13 gives the $v_0$ ($\Delta Abs_{482}$/min) and $v_0/v_{0max}$ (%) measured as a function of aztreonam and ampicillin-fluorescein (ampi-flu) concentrations.

TABLE 13

| | Aztreonam (standard curve) | | Ampi-flu (standard curve) | |
|---|---|---|---|---|
| mg/L | $v_0$ ($\Delta Abs482$/min) | $v_0/v_{0max}$ | $v_0$ ($\Delta Abs482$/min) | $v_0/v_{0max}$ |
| 0 | 0.3369 | 100% | 0.2697 | 100% |
| 0.1 | 0.3204 | 95% | 0.2638 | 98% |
| 0.5 | 0.2597 | 77% | 0.2336 | 87% |
| 1.5 | 0.1575 | 47% | 0.169 | 63% |
| 3 | 0.0795 | 24% | 0.1064 | 39% |
| 5 | 0.0362 | 11% | 0.063 | 23% |
| 7.5 | 0.0155 | 5% | 0.0389 | 14% |
| 10 | 0.0076 | 2% | 0.025 | 9% |

Table 14 gives the calculated and expected concentrations of aztreonam in sample 1, ampicillin-fluorescein (ampi-flu) in sample 2, and aztreonam and ampicillin-fluorescein (ampi-flu) in sample 3.

TABLE 14

|  | Sample 1 Aztreonam C18 fraction 10% | Sample 2 Ampi-flu C18 fraction 10% | Sample 3 Mix C18 fraction 10% | Sample 3 Mix no C18 separation |
|---|---|---|---|---|
| $v_{0max}$ ($\Delta Abs_{482}$/min) | 0.3291 | 0.3278 | 0.3287 | 0.3218 |
| $v_0$ ($\Delta Abs_{482}$/min) | 0.1424 | 0.3281 | 0.1439 | 0.0831 |
| $v_0/v_{0max}$ | 43% | 100% | 44% | 26% |
| Calculated aztreonam (mg/L) * | 48.7 | — | 48.1 | — |
| Expected aztreonam (mg/L) | 50 | — | 50 | — |
| Calculated ampi-flu (mg/L) ** | — | — | — | 49.7 |
| Expected ampi-flu (mg/L) | — | — | — | 50 |

* 500 μl of aztreonam solution was collected in 1 ml after C18 separation (fraction 10% acetonitrile) and this fraction was diluted 15-fold before the dosage. so the correction factor was 30. Concentrations were extrapolated using the standard curve of aztreonam.
** The sample 3 before the separation (no C18 separation) was diluted 30-fold and dosed. From equation 3. it was calculated that the $v_0/v_{0max}$ due to ampi-flu was 59% (44% × 59% = 26%). Concentration of ampi-flu in sample 3 was extrapolated using the standard curve of ampi-flu.

(*) 500 μl of aztreonam solution was collected in 1 ml after C18 separation (fraction 10% acetonitrile) and this fraction was diluted 15-fold before the dosage, so the correction factor was 30. Concentrations were extrapolated using the standard curve of aztreonam.

(**) The sample 3 before the separation (no C18 separation) was diluted 30-fold and dosed. From equation 3, it was calculated that the $v_0/v_{0max}$ due to ampi-flu was 59% (44%× 59%=26%). Concentration of ampi-flu in sample 3 was extrapolated using the standard curve of ampi-flu.

Conclusively, in a mixture of two beta-lactams antibiotics, the individual concentration of each beta-lactam antibiotic was determined using a class C beta-lactamase such as class C beta-lactamase of *Enterobacter cloacae* P99 with the help of a separation method.

It is to be understood that although preferred embodiments and/or materials have been discussed for providing embodiments according to the present invention, various modifications or changes may be made without departing from the scope and spirit of this invention.

The invention claimed is:

1. A method for determining concentration of a free beta-lactam antibiotic in a biological sample, comprising the steps of:
   (a) providing at least one class C beta-lactamase comprising an amino acid sequence selected from the group consisting of SEQ ID NO:6, SEQ ID NO:8, SEQ ID NO:10 and SEQ ID NO:12;
   (b) providing at least one biological sample;
   (c) contacting said at least one class C beta-lactamase with said at least one biological sample; and
   (d) determining said concentration of said free beta-lactam antibiotic in said at least one biological sample.

2. A method for determining concentration of a free beta-lactam antibiotic in a biological sample, comprising the steps of:
   (a) providing at least one class C beta-lactamase comprising an amino acid sequence of SEQ ID NO:8 or SEQ ID NO:12;
   (b) providing at least one biological sample;
   (c) contacting said at least one class C beta-lactamase with said at least one biological sample; and
   (d) determining said concentration of said free beta-lactam antibiotic in said at least one biological sample.

3. The method according to claim 1, wherein said biological sample is selected from the group comprising serum, blood, urine, interstitial fluid, saliva, tears, exudates, fluid collected from a deep tissue, fluid collected from a subcutaneous tissue.

4. The method of claim 3, wherein said biological sample is serum.

5. The method according to claim 1, wherein said biological sample is obtained from a subject receiving an antibiotherapy.

6. The method according to claim 1, wherein said biological sample is obtained from a subject being treated for an infection caused by Gram positive and/or Gram negative micro-organisms.

7. The method according to claim 2, wherein said biological sample is selected from the group comprising serum, blood, urine, interstitial fluid, saliva, tears, exudates, fluid collected from a deep tissue, fluid collected from a subcutaneous tissue, preferably said biological sample is serum.

8. The method of claim 7, wherein said biological sample is serum.

9. The method according to claim 2, wherein said biological sample is obtained from a subject receiving an antibiotherapy.

10. The method according to claim 2, wherein said biological sample is obtained from a subject being treated for an infection caused by Gram positive and/or Gram negative micro-organisms.

* * * * *

SEQUENCE LISTING

<160> NUMBER OF SEQ ID NOS: 12

<210> SEQ ID NO 1
<211> LENGTH: 27
<212> TYPE: DNA
<213> ORGANISM: Artificial
<220> FEATURE:
<223> OTHER INFORMATION: Primer

<400> SEQUENCE: 1
aaccatggcg ccagtgtcag aaaaaca                              27

<210> SEQ ID NO 2
<211> LENGTH: 31
<212> TYPE: DNA
<213> ORGANISM: Artificial
<220> FEATURE:
<223> OTHER INFORMATION: Primer

<400> SEQUENCE: 2
aactcgagcg cctcaaggat atggtatgcc g                         31

<210> SEQ ID NO 3
<211> LENGTH: 36
<212> TYPE: DNA
<213> ORGANISM: Artificial
<220> FEATURE:
<223> OTHER INFORMATION: Primer

<400> SEQUENCE: 3
ccggagaacg ttgctgattg ctcacttaag cagggc                    36

<210> SEQ ID NO 4
<211> LENGTH: 36
<212> TYPE: DNA
<213> ORGANISM: Artificial

```
<220> FEATURE:
<223> OTHER INFORMATION: Primer

<400> SEQUENCE: 4
gccctgctta agtgagcaat cagcaacgtt ctccgg                                    36

<210> SEQ ID NO 5
<211> LENGTH: 1107
<212> TYPE: DNA
<213> ORGANISM: Artificial
<220> FEATURE:
<223> OTHER INFORMATION: Recombinant DNA

<400> SEQUENCE: 5
atggcgccag tgtcagaaaa acagctggcg gaggtggtcg cgaatacgat taccccgctg       60
atgaaagccc agtctgttcc aggcatggcg gtggccgtta tttatcaggg aaaaccgcac      120
tattacacat ttggcaaggc cgatatcgcg gcgaataaac ccgttacgcc tcagaccctg      180
ttcgagctgg gttctataag taaaaccttc accggcgttt taggtgggga tgccattgct      240
cgcggtgaaa tttcgctgga cgatgcggtg accagatact ggccacagct gacgggcaag      300
cagtggcagg gtattcgtat gctggatctc gccacctaca ccgctggcgg cctgccgcta      360
caggtaccgg atgaggtcac ggataacgcc tccctgctgc gcttttatca aaactggcag      420
ccgcagtgga agcctggcac aacgcgtctt tacgccaacg ccagcatcgg tcttttttggt     480 gcgctggcgg tcaaaccttc tggcatgccc tatgagcagg ccatgacgac gcgggtcctt      540
aagccgctca agctggacca tacctggatt aacgtgccga aagcggaaga ggcgcattac      600
gcctggggct atcgtgacgg taaagcggtg cgcgtttcgc cgggtatgct ggatgcacaa      660
gcctatggcg tgaaaaccaa cgtgcaggat atgcgaact  gggtcatggc aaacatggcg      720
ccggagaacg ttgctgatgc ctcacttaag cagggcatcg cgctggcgca gtcgcgctac      780
tggcgtatcg ggtcaatgta tcagggtctg ggctgggaga tgctcaactg gcccgtggag      840
gccaacacgg tggtcgaggg cagcgacagt aaggtagcac tggcgccgtt gcccgtggca      900
gaagtgaatc caccggctcc cccggtcaaa gcgtcctggg tccataaaac gggctctact      960
ggcgggtttg gcagctacgt ggcctttatt cctgaaaagc agatcggtat tgtgatgctc     1020
gcgaatacaa gctatccgaa cccggcacgc gttgaggcgg cataccatat ccttgaggcg     1080
ctcgagcacc accaccacca ccactga                                         1107

<210> SEQ ID NO 6
<211> LENGTH: 368
<212> TYPE: PRT
<213> ORGANISM: Artificial
<220> FEATURE:
<223> OTHER INFORMATION: Recombinant protein

<400> SEQUENCE: 6
```

Met Ala Pro Val Ser Glu Lys Gln Leu Ala Glu Val Val Ala Asn Thr
1               5                   10                  15

Ile Thr Pro Leu Met Lys Ala Gln Ser Val Pro Gly Met Ala Val Ala
            20                  25                  30

Val Ile Tyr Gln Gly Lys Pro His Tyr Tyr Thr Phe Gly Lys Ala Asp
        35                  40                  45

Ile Ala Ala Asn Lys Pro Val Thr Pro Gln Thr Leu Phe Glu Leu Gly
    50                  55                  60

Ser Ile Ser Lys Thr Phe Thr Gly Val Leu Gly Gly Asp Ala Ile Ala
65                  70                  75                  80

```
Arg Gly Glu Ile Ser Leu Asp Asp Ala Val Thr Arg Tyr Trp Pro Gln
                85                  90                  95

Leu Thr Gly Lys Gln Trp Gln Gly Ile Arg Met Leu Asp Leu Ala Thr
            100                 105                 110

Tyr Thr Ala Gly Gly Leu Pro Leu Gln Val Pro Asp Glu Val Thr Asp
        115                 120                 125

Asn Ala Ser Leu Leu Arg Phe Tyr Gln Asn Trp Gln Pro Gln Trp Lys
    130                 135                 140

Pro Gly Thr Thr Arg Leu Tyr Ala Asn Ala Ser Ile Gly Leu Phe Gly
145                 150                 155                 160

Ala Leu Ala Val Lys Pro Ser Gly Met Pro Tyr Glu Gln Ala Met Thr
                165                 170                 175

Thr Arg Val Leu Lys Pro Leu Lys Leu Asp His Thr Trp Ile Asn Val
            180                 185                 190

Pro Lys Ala Glu Glu Ala His Tyr Ala Trp Gly Tyr Arg Asp Gly Lys
        195                 200                 205

Ala Val Arg Val Ser Pro Gly Met Leu Asp Ala Gln Ala Tyr Gly Val
    210                 215                 220

Lys Thr Asn Val Gln Asp Met Ala Asn Trp Val Met Ala Asn Met Ala
225                 230                 235                 240

Pro Glu Asn Val Ala Asp Ala Ser Leu Lys Gln Gly Ile Ala Leu Ala
                245                 250                 255

Gln Ser Arg Tyr Trp Arg Ile Gly Ser Met Tyr Gln Gly Leu Gly Trp
            260                 265                 270

Glu Met Leu Asn Trp Pro Val Glu Ala Asn Thr Val Val Glu Gly Ser
        275                 280                 285

Asp Ser Lys Val Ala Leu Ala Pro Leu Pro Val Ala Glu Val Asn Pro
    290                 295                 300

Pro Ala Pro Pro Val Lys Ala Ser Trp Val His Lys Thr Gly Ser Thr
305                 310                 315                 320

Gly Gly Phe Gly Ser Tyr Val Ala Phe Ile Pro Glu Lys Gln Ile Gly
                325                 330                 335

Ile Val Met Leu Ala Asn Thr Ser Tyr Pro Asn Pro Ala Arg Val Glu
            340                 345                 350

Ala Ala Tyr His Ile Leu Glu Ala Leu Glu His His His His His His
        355                 360                 365

<210> SEQ ID NO 7
<211> LENGTH: 1107
<212> TYPE: DNA
<213> ORGANISM: Artificial
<220> FEATURE:
<223> OTHER INFORMATION: variant of P99

<400> SEQUENCE: 7
atggcgccag tgtcagaaaa acagctggcg gaggtggtcg cgaatacgat taccccgctg      60
atgaaagccc agtctgttcc aggcatggcg gtggccgtta tttatcaggg aaaaccgcac     120
tattacacat ttggcaaggc cgatatcgcg gcgaataaac ccgttacgcc tcagaccctg     180
ttcgagctgg gttctataag taaaaccttc accggcgttt taggtgggga tgccattgct     240
cgcggtgaaa tttcgctgga cgatgcggtg accagatact ggccacagct gacgggcaag     300
cagtggcagg gtattcgtat gctggatctc gccacctaca ccgctggcgg cctgccgcta     360
caggtaccgg atgaggtcac ggataacgcc tccctgctgc gcttttatca aaactggcag     420
```

-continued

```
ccgcagtgga agcctggcac aacgcgtctt tacgccaacg ccagcatcgg tcttttttggt    480
gcgctggcgg tcaaaccttc tggcatgccc tatgagcagg ccatgacgac gcgggtcctt    540
aagccgctca agctggacca tacctggatt aacgtgccga agcggaaga ggcgcattac     600
gcctggggct atcgtgacgg taaagcggtg cgcgtttcgc cgggtatgct ggatgcacaa    660
gcctatggcg tgaaaaccaa cgtgcaggat atggcgaact gggtcatggc aaacatggcg    720
ccggagaacg ttgctgattg ctcacttaag cagggcatcg cgctggcgca gtcgcgctac    780
tggcgtatcg ggtcaatgta tcagggtctg gctgggaga tgctcaactg gcccgtggag     840
gccaacacgg tggtcgaggg cagcgacagt aaggtagcac tggcgccgtt gcccgtggca    900
gaagtgaatc caccggctcc cccggtcaaa gcgtcctggg tccataaaac gggctctact    960
ggcgggtttg gcagctacgt ggcctttatt cctgaaaagc agatcggtat tgtgatgctc   1020
gcgaatacaa gctatccgaa cccggcacgc gttgaggcgg cataccatat ccttgaggcg   1080
ctcgagcacc accaccacca ccactga                                       1107

<210> SEQ ID NO 8
<211> LENGTH: 368
<212> TYPE: PRT
<213> ORGANISM: Artificial
<220> FEATURE:
<223> OTHER INFORMATION: variant of P99

<400> SEQUENCE: 8

Met Ala Pro Val Ser Glu Lys Gln Leu Ala Glu Val Val Ala Asn Thr
1               5                   10                  15

Ile Thr Pro Leu Met Lys Ala Gln Ser Val Pro Gly Met Ala Val Ala
            20                  25                  30

Val Ile Tyr Gln Gly Lys Pro His Tyr Tyr Thr Phe Gly Lys Ala Asp
        35                  40                  45

Ile Ala Ala Asn Lys Pro Val Thr Pro Gln Thr Leu Phe Glu Leu Gly
    50                  55                  60

Ser Ile Ser Lys Thr Phe Thr Gly Val Leu Gly Gly Asp Ala Ile Ala
65                  70                  75                  80

Arg Gly Glu Ile Ser Leu Asp Asp Ala Val Thr Arg Tyr Trp Pro Gln
                85                  90                  95

Leu Thr Gly Lys Gln Trp Gln Gly Ile Arg Met Leu Asp Leu Ala Thr
            100                 105                 110

Tyr Thr Ala Gly Gly Leu Pro Leu Gln Val Pro Asp Glu Val Thr Asp
        115                 120                 125

Asn Ala Ser Leu Leu Arg Phe Tyr Gln Asn Trp Gln Pro Gln Trp Lys
    130                 135                 140

Pro Gly Thr Thr Arg Leu Tyr Ala Asn Ala Ser Ile Gly Leu Phe Gly
145                 150                 155                 160

Ala Leu Ala Val Lys Pro Ser Gly Met Pro Tyr Glu Gln Ala Met Thr
                165                 170                 175

Thr Arg Val Leu Lys Pro Leu Lys Leu Asp His Thr Trp Ile Asn Val
            180                 185                 190

Pro Lys Ala Glu Glu Ala His Tyr Ala Trp Gly Tyr Arg Asp Gly Lys
        195                 200                 205

Ala Val Arg Val Ser Pro Gly Met Leu Asp Ala Gln Ala Tyr Gly Val
    210                 215                 220

Lys Thr Asn Val Gln Asp Met Ala Asn Trp Val Met Ala Asn Met Ala
225                 230                 235                 240
```

Pro Glu Asn Val Ala Asp Cys Ser Leu Lys Gln Gly Ile Ala Leu Ala
            245                 250                 255

Gln Ser Arg Tyr Trp Arg Ile Gly Ser Met Tyr Gln Gly Leu Gly Trp
        260                 265                 270

Glu Met Leu Asn Trp Pro Val Glu Ala Asn Thr Val Val Glu Gly Ser
    275                 280                 285

Asp Ser Lys Val Ala Leu Ala Pro Leu Pro Val Ala Glu Val Asn Pro
290                 295                 300

Pro Ala Pro Pro Val Lys Ala Ser Trp Val His Lys Thr Gly Ser Thr
305                 310                 315                 320

Gly Gly Phe Gly Ser Tyr Val Ala Phe Ile Pro Glu Lys Gln Ile Gly
            325                 330                 335

Ile Val Met Leu Ala Asn Thr Ser Tyr Pro Asn Pro Ala Arg Val Glu
        340                 345                 350

Ala Ala Tyr His Ile Leu Glu Ala Leu Glu His His His His His His
    355                 360                 365

<210> SEQ ID NO 9
<211> LENGTH: 1146
<212> TYPE: DNA
<213> ORGANISM: Enterobacter cloacae

<400> SEQUENCE: 9
atgatgagaa atcccttttg ctgcgccctg ctgctcggca tctcttgctc tgctctcgcc      60
acgccagtgt cagaaaaaca gctggcggag gtggtcgcga atacgattac cccgctgatg     120
aaagcccagt ctgttccagg catggcgtg gccgttattt atcagggaaa accgcactat      180
tacacatttg gcaaggccga tatcgcggcg aataaacccg ttacgcctca gaccctgttc     240
gagctgggtt ctataagtaa aaccttcacc ggcgttttag gtggggatgc cattgctcgc     300
ggtgaaattt cgctggacga tgcggtgacc agatactggc acagctgac gggcaagcag      360 tggcagggta ttcgtatgct ggatctcgcc acctacaccg ctggcggcct gccgctacag     420
gtaccggatg aggtcacgga taacgcctcc ctgctgcgct tttatcaaaa ctggcagccg     480
cagtggaagc ctggcacaac gcgtctttac gccaacgcca gcatcggtct ttttggtgcg     540
ctggcggtca accttctgg catgccctat gagcaggcca tgacgacgcg ggtccttaag      600
ccgctcaagc tggaccatac ctggattaac gtgccgaaag cggaagaggc gcattacgcc     660
tggggctatc gtgacggtaa agcggtgcgc gtttcgccgg gtatgctgga tgcacaagcc     720 tatgcgtga aaaccaacgt gcaggatatg cgaactggg tcatggcaaa catggcgccg       780
gagaacgttg ctgatgcctc acttaagcag ggcatcgcgc tggcgcagtc gcgctactgg     840
cgtatcgggt caatgtatca gggtctgggc tgggagatgc tcaactgcc cgtgaggcc      900 aacacggtgg tcgagggcag cgacagtaag gtagcactgg cgccgttgcc cgtggcagaa     960
gtgaatccac cggctccccc ggtcaaagcg tcctgggtcc ataaaacggg ctctactggc    1020
gggtttggca gctacgtggc ctttattcct gaaaagcaga tcggtattgt gatgctcgcg    1080
aatacaagct atccgaaccc ggcacgcgtt gaggcggcat accatatcct cgaggcgcta    1140
cagtaa                                                              1146

<210> SEQ ID NO 10
<211> LENGTH: 381
<212> TYPE: PRT
<213> ORGANISM: Enterobacter cloacae

<400> SEQUENCE: 10

```
Met Met Arg Lys Ser Leu Cys Cys Ala Leu Leu Gly Ile Ser Cys
1               5                   10                  15

Ser Ala Leu Ala Thr Pro Val Ser Glu Lys Gln Leu Ala Glu Val Val
            20                  25                  30

Ala Asn Thr Ile Thr Pro Leu Met Lys Ala Gln Ser Val Pro Gly Met
            35                  40                  45

Ala Val Ala Val Ile Tyr Gln Gly Lys Pro His Tyr Tyr Thr Phe Gly
        50                  55                  60

Lys Ala Asp Ile Ala Ala Asn Lys Pro Val Thr Pro Gln Thr Leu Phe
65                  70                  75                  80

Glu Leu Gly Ser Ile Ser Lys Thr Phe Thr Gly Val Leu Gly Gly Asp
                85                  90                  95

Ala Ile Ala Arg Gly Glu Ile Ser Leu Asp Asp Ala Val Thr Arg Tyr
            100                 105                 110

Trp Pro Gln Leu Thr Gly Lys Gln Trp Gln Gly Ile Arg Met Leu Asp
        115                 120                 125

Leu Ala Thr Tyr Thr Ala Gly Gly Leu Pro Leu Gln Val Pro Asp Glu
130                 135                 140

Val Thr Asp Asn Ala Ser Leu Leu Arg Phe Tyr Gln Asn Trp Gln Pro
145                 150                 155                 160

Gln Trp Lys Pro Gly Thr Thr Arg Leu Tyr Ala Asn Ala Ser Ile Gly
            165                 170                 175

Leu Phe Gly Ala Leu Ala Val Lys Pro Ser Gly Met Pro Tyr Glu Gln
        180                 185                 190

Ala Met Thr Thr Arg Val Leu Lys Pro Leu Lys Leu Asp His Thr Trp
    195                 200                 205

Ile Asn Val Pro Lys Ala Glu Glu Ala His Tyr Ala Trp Gly Tyr Arg
210                 215                 220

Asp Gly Lys Ala Val Arg Val Ser Pro Gly Met Leu Asp Ala Gln Ala
225                 230                 235                 240

Tyr Gly Val Lys Thr Asn Val Gln Asp Met Ala Asn Trp Val Met Ala
            245                 250                 255

Asn Met Ala Pro Glu Asn Val Ala Asp Ala Ser Leu Lys Gln Gly Ile
        260                 265                 270

Ala Leu Ala Gln Ser Arg Tyr Trp Arg Ile Gly Ser Met Tyr Gln Gly
    275                 280                 285

Leu Gly Trp Glu Met Leu Asn Trp Pro Val Glu Ala Asn Thr Val Val
290                 295                 300

Glu Gly Ser Asp Ser Lys Val Ala Leu Ala Pro Leu Pro Val Ala Glu
305                 310                 315                 320

Val Asn Pro Pro Ala Pro Pro Val Lys Ala Ser Trp Val His Lys Thr
            325                 330                 335

Gly Ser Thr Gly Gly Phe Gly Ser Tyr Val Ala Phe Ile Pro Glu Lys
        340                 345                 350

Gln Ile Gly Ile Val Met Leu Ala Asn Thr Ser Tyr Pro Asn Pro Ala
    355                 360                 365

Arg Val Glu Ala Ala Tyr His Ile Leu Glu Ala Leu Gln
370                 375                 380

<210> SEQ ID NO 11
<211> LENGTH: 1146
<212> TYPE: DNA
<213> ORGANISM: Artificial
<220> FEATURE:
```

<223> OTHER INFORMATION: Variant of P99

<400> SEQUENCE: 11

```
atgatgagaa atccctttg ctgcgccctg ctgctcggca tctcttgctc tgctctcgcc      60
acgccagtgt cagaaaaaca gctggcggag gtggtcgcga atacgattac cccgctgatg     120
aaagcccagt ctgttccagg catggcggtg gccgttattt atcagggaaa accgcactat     180
tacacatttg gcaaggccga tatcgcggcg aataaacccg ttacgcctca gaccctgttc     240
gagctgggtt ctataagtaa aaccttcacc ggcgttttag gtgggatgc cattgctcgc      300
ggtgaaattt cgctggacga tgcggtgacc agatactggc cacagctgac gggcaagcag     360
tggcagggta ttcgtatgct ggatctcgcc acctacaccg ctggcggcct gccgctacag     420
gtaccggatg aggtcacgga taacgcctcc ctgctgcgct tttatcaaaa ctggcagccg     480
cagtggaagc ctggcacaac gcgtctttac gccaacgcca gcatcggtct ttttggtgcg     540
ctggcggtca aaccttctgg catgcccat gagcaggcca tgacgacgcg ggtccttaag      600
ccgctcaagc tggaccatac ctggattaac gtgccgaaag cggaagaggc gcattacgcc     660
tggggctatc gtgacggtaa agcggtgcgc gtttcgccgg tatgctgga tgcacaagcc      720
tatgcgtga aaccaacgt gcaggatatg gcgaactggg tcatggcaaa catggcgccg       780
gagaacgttg ctgattgctc acttaagcag ggcatcgcgc tggcgcagtc gcgctactgg     840
cgtatcgggt caatgtatca gggtctgggc tgggagatgc tcaactggcc cgtggaggcc     900
aacacggtgg tcgagggcag cgacagtaag gtagcactgg cgccgttgcc cgtggcagaa     960
gtgaatccac cggctccccc ggtcaaagcg tcctgggtcc ataaaacggg ctctactggc    1020
gggtttggca gctacgtggc ctttattcct gaaaagcaga tcggtattgt gatgctcgcg    1080
aatacaagct atccgaaccc ggcacgcgtt gaggcggcat accatatcct cgaggcgcta    1140
cagtaa                                                                1146
```

<210> SEQ ID NO 12
<211> LENGTH: 381
<212> TYPE: PRT
<213> ORGANISM: Artificial
<220> FEATURE:
<223> OTHER INFORMATION: Variant of P99

<400> SEQUENCE: 12

```
Met Met Arg Lys Ser Leu Cys Cys Ala Leu Leu Leu Gly Ile Ser Cys
1               5                   10                  15

Ser Ala Leu Ala Thr Pro Val Ser Glu Lys Gln Leu Ala Glu Val Val
            20                  25                  30

Ala Asn Thr Ile Thr Pro Leu Met Lys Ala Gln Ser Val Pro Gly Met
        35                  40                  45

Ala Val Ala Val Ile Tyr Gln Gly Lys Pro His Tyr Tyr Thr Phe Gly
    50                  55                  60

Lys Ala Asp Ile Ala Ala Asn Lys Pro Val Thr Pro Gln Thr Leu Phe
65                  70                  75                  80

Glu Leu Gly Ser Ile Ser Lys Thr Phe Thr Gly Val Leu Gly Gly Asp
                85                  90                  95

Ala Ile Ala Arg Gly Glu Ile Ser Leu Asp Asp Ala Val Thr Arg Tyr
            100                 105                 110

Trp Pro Gln Leu Thr Gly Lys Gln Trp Gln Gly Ile Arg Met Leu Asp
        115                 120                 125

Leu Ala Thr Tyr Thr Ala Gly Gly Leu Pro Leu Gln Val Pro Asp Glu
```

```
                    130                 135                 140
Val Thr Asp Asn Ala Ser Leu Leu Arg Phe Tyr Gln Asn Trp Gln Pro
145                 150                 155                 160

Gln Trp Lys Pro Gly Thr Thr Arg Leu Tyr Ala Asn Ala Ser Ile Gly
                165                 170                 175

Leu Phe Gly Ala Leu Ala Val Lys Pro Ser Gly Met Pro Tyr Glu Gln
            180                 185                 190

Ala Met Thr Thr Arg Val Leu Lys Pro Leu Lys Leu Asp His Thr Trp
            195                 200                 205

Ile Asn Val Pro Lys Ala Glu Glu Ala His Tyr Ala Trp Gly Tyr Arg
        210                 215                 220

Asp Gly Lys Ala Val Arg Val Ser Pro Gly Met Leu Asp Ala Gln Ala
225                 230                 235                 240

Tyr Gly Val Lys Thr Asn Val Gln Asp Met Ala Asn Trp Val Met Ala
                245                 250                 255

Asn Met Ala Pro Glu Asn Val Ala Asp Cys Ser Leu Lys Gln Gly Ile
            260                 265                 270

Ala Leu Ala Gln Ser Arg Tyr Trp Arg Ile Gly Ser Met Tyr Gln Gly
            275                 280                 285

Leu Gly Trp Glu Met Leu Asn Trp Pro Val Glu Ala Asn Thr Val Val
        290                 295                 300

Glu Gly Ser Asp Ser Lys Val Ala Leu Ala Pro Leu Pro Val Ala Glu
305                 310                 315                 320

Val Asn Pro Pro Ala Pro Pro Val Lys Ala Ser Trp Val His Lys Thr
                325                 330                 335

Gly Ser Thr Gly Gly Phe Gly Ser Tyr Val Ala Phe Ile Pro Glu Lys
            340                 345                 350

Gln Ile Gly Ile Val Met Leu Ala Asn Thr Ser Tyr Pro Asn Pro Ala
            355                 360                 365

Arg Val Glu Ala Ala Tyr His Ile Leu Glu Ala Leu Gln
370                 375                 380
```